(12) United States Patent
McReynolds et al.

(10) Patent No.: US 8,753,809 B2
(45) Date of Patent: Jun. 17, 2014

(54) METHODS AND COMPOSITIONS FOR DETECTION AND ENRICHMENT OF TARGET SMALL RNAS

(71) Applicant: New England Biolabs, Inc., Ipswich, MA (US)

(72) Inventors: Larry A. McReynolds, Beverly, MA (US); Jingmin Jin, Middleton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 13/723,556

(22) Filed: Dec. 21, 2012

(65) Prior Publication Data

US 2013/0109018 A1    May 2, 2013

Related U.S. Application Data

(62) Division of application No. 12/738,580, filed as application No. PCT/US2008/081520 on Oct. 29, 2008, now abandoned.

(60) Provisional application No. 60/983,503, filed on Oct. 29, 2007.

(51) Int. Cl.
*C12Q 1/68* (2006.01)

(52) U.S. Cl.
USPC .............. 435/6; 435/325; 435/375; 536/24.5

(58) Field of Classification Search
CPC combination set(s) only.
See application file for complete search history.

(56) References Cited

U.S. PATENT DOCUMENTS

| 5,643,758 | A  | 7/1997 | Guan et al. |
| 2004/0115130 | A1 | 6/2004 | Johnsson et al. |
| 2006/0024775 | A1 | 2/2006 | Kindermann et al. |
| 2006/0035333 | A1 | 2/2006 | Taron et al. |
| 2006/0292651 | A1 | 12/2006 | Juillerat et al. |
| 2007/0082336 | A1 | 4/2007 | Johnsson et al. |
| 2007/0207532 | A1 | 9/2007 | Barnikov et al. |
| 2007/0243568 | A1 | 10/2007 | Jaccard et al. |

FOREIGN PATENT DOCUMENTS

WO    2006/032713    3/2006

OTHER PUBLICATIONS

Cattoli et al. (Biotechnol. Prog. 2002, vol. 18: 94-100).*
Safrik et al. (BioMagnetic Research 2004, 2:7).*
Silhavy et al. Embo J. 21:3070-80 (2002).
Vester & Wengel Biochemistry 43(42):13233-41 (2004).
Yezhelyev et al. J Am Chem Soc. 130(28):9006-12 (2008).
Calabrese, et al., RNA, 12:2092-2102 (2006).
Jacobs, et al., Methods, 15:225-232 (1998).
Vargason, et al., Cell, 115:799-811 (2003).
International Search Report for PCT/US2008/081520, mailed Jan. 28, 2009.
Cheng et al Biochim Biophys Acta 1774 12 1528-1535 2007.
Lakatos et al EMBO Jour 25 12 2768-2780 2006.
Alvarez-Garcia et al. Development 132:4653-4662 (2005).
Esquela-Kerscher & Slack Nature Reviews Cancer 6:259-269 (2006).
Lundblad et al. Mol. Endocrinol 10:607-612 (1996).

* cited by examiner

*Primary Examiner* — Kimberly Chong
(74) *Attorney, Agent, or Firm* — New England Biolabs, Inc; Harriet M. Strimpel

(57) ABSTRACT

Methods and compositions are provided for detecting small target RNAs where the target RNA may be single-stranded or double-stranded and may be contained in a mixture of RNAs of different types and sizes. The methods and compositions utilize a p19 fusion protein that is capable of binding double-stranded RNA in a size-specific but sequence-independent manner and is further capable of binding to a matrix such as beads or plastic microwell plates. By labeling the p19 fusion protein or the target RNA in a polynucleotide duplex either directly or indirectly, low levels of target RNA including microRNAs can be detected from cells. This can be applied to diagnosis of pathological conditions.

19 Claims, 20 Drawing Sheets

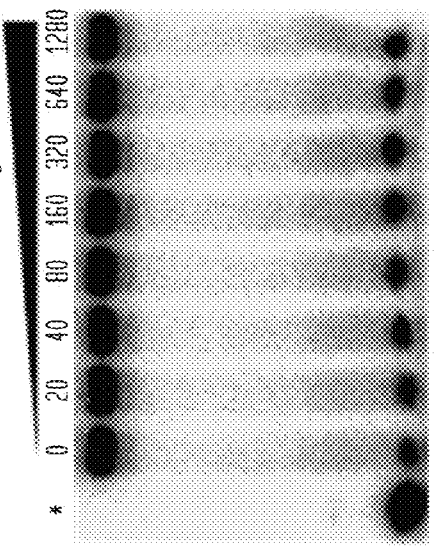
FIG. 5B 21 mer dsDNA (ng)
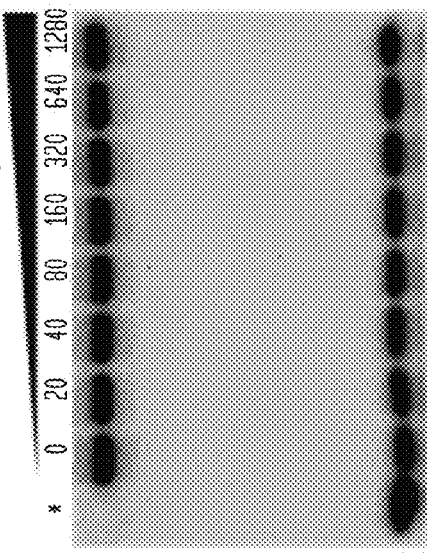
FIG. 5D 21 mer ssRNA (ng)
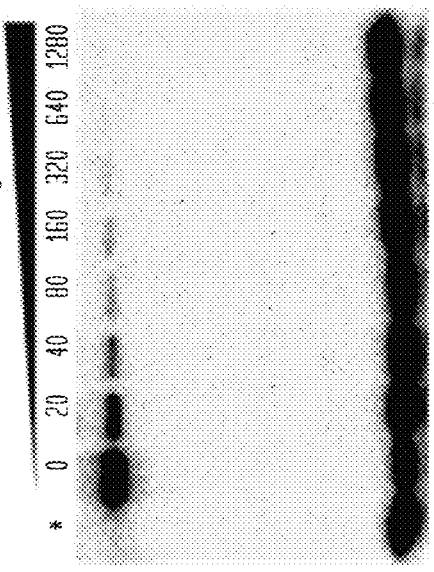
FIG. 5A 21 mer dsRNA (ng)
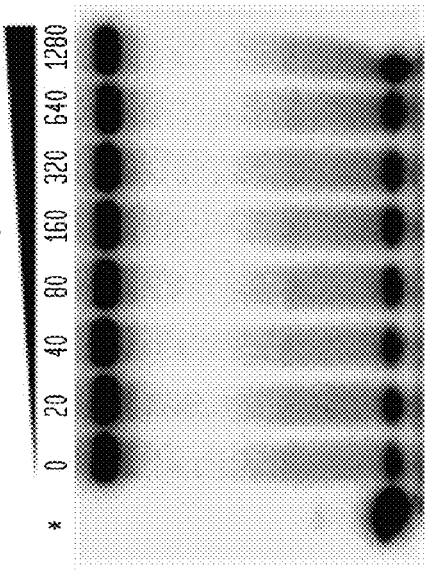
FIG. 5C rRNA (ng)

FIG. 7

| | | | STRUCTURE | RELATIVE AFFINITY |
|---|---|---|---|---|
| 1 | 21-mer ds siRNA | 5' pCGUACGCGGAAUACUUCGAUU 3' (SEQ ID NO:4)<br>3' UUGCAUGCGCCUUAUGAAGCUp 5' (SEQ ID NO:5) | p▬▬▬▬<br>▬▬▬▬p | 1 |
| 2 | 17-mer ds RNA | 5' pCUCAACCAGCCACUGCU 3' (SEQ ID NO:6)<br>3' UAGAGUUGGUCGGUGACp 5' (SEQ ID NO:7) | p▬▬▬<br>▬▬▬p | 106 |
| 3 | 25-mer ds RNA | 5' pCGUACGCGGAAUACUUCGAAAUGUU 3' (SEQ ID NO:8)<br>3' UUGCAUGCGCCUUAUGAAGCUUUACp 5' (SEQ ID NO:9) | p▬▬▬▬▬<br>▬▬▬▬▬p | 230 |
| 4 | 21-mer ds RNA (w/o 5'p) | 5' CGUACGCGGAAUACUUCGAUU 3' (SEQ ID NO:10)<br>3' UUGCAUGCGCCUUAUGAAGCU 5' (SEQ ID NO:11) | ▬▬▬▬<br>▬▬▬▬ | 44 |
| 5 | 21-mer ds RNA (5'ppp) | 5' pppCGUACGCGGAAUACUUCGAUU 3' (SEQ ID NO:12)<br>3' UUGCAUGCGCCUUAUGAAGCUppp 5' (SEQ ID NO:13) | ppp▬▬▬▬<br>▬▬▬▬ppp | 8 |
| 6 | 19-mer blunt ds RNA | 5' pCGUACGCGGAAUACUUCGA 3' (SEQ ID NO:14)<br>3' GCAUGCGCCUUAUGAAGCUp 5' | p▬▬▬<br>▬▬▬p | 0.3 |
| 7 | 20-mer blunt ds RNA | 5' pACGUACGCGGAAUACUUCGAU 3' (SEQ ID NO:15)<br>3' UGCAUGCGCCUUAUGAAGCUAp 5' | p▬▬▬▬<br>▬▬▬▬p | 0.6 |
| 8 | 21-mer blunt ds RNA | 5' pACGUACGCGGAAUACUUCGAUU 3'<br>3' UUGCAUGCGCCUUAUGAAGCUAp 5' | p▬▬▬▬<br>▬▬▬▬p | 8.6 |
| 9 | 21-mer ds RNA/DNA | 5' pCGUACGCGGAAUACUUCGAUU 3' (SEQ ID NO:16)<br>3' TTGCATGCGCCTTATGAAGCTp 5' (SEQ ID NO:17) | p▬▬▬▬<br>▬▬▬▬p | 61 |
| 10 | 21-mer ds DNA | 5' pCGTACGCGGAATACTTCGATT 3' (SEQ ID NO:18)<br>3' TTGCATGCGCCTTATGAAGCTp 5' (SEQ ID NO:19) | p▬▬▬▬<br>▬▬▬▬p | >1000 |
| 11 | 21-mer ds RNA-FAM | 5' pCGUACGCGGCCUUAU(FAM)GAAGCU 3' (SEQ ID NO:20)<br>3' UUGCAUGCGCCUUAU(FAM)GAAGCUp 5' (SEQ ID NO:21) | p▬▬●▬<br>▬▬●▬p | 1.3 |
| 12 | 21-mer ss RNA | 5' pCGUACGCGGAAUACUUCGAUU 3' (SEQ ID NO:22) | p▬▬▬▬ | >1000 |
| 13 | cel-let-7 ds microRNA | 5' pUGAGGUAGUAGGUUGUAUAGU 3' (SEQ ID NO:23)<br>3' CCAUUCAUCCAUUCAUAAGUACp 5' (SEQ ID NO:24) | p▬▬▬▬<br>▬▬▬▬p | 20 |
| 14 | gga-let-7 ds microRNA | 5' pGAGGUAGUAGGUUGCAUAGU 3' (SEQ ID NO:25)<br>3' UCU-UCCGUCGUCCAACAUAU 5' (SEQ ID NO:26) | p▬▬ ▬ ▬<br>▬ ▬ ▬ ▬ | 75 |
| 15 | cel-mir-45 ds microRNA | 5' pUGACUA--GAGACACAUUCAGCU 3' (SEQ ID NO:27)<br>3' AUACUGAUUGCUC-GUGUAGGUCp 5' (SEQ ID NO:28) | p▬▬}▬<br>▬▬{▬p | 37 |
| 16 | rRNA (rat liver ribosomal RNA) | | | >1000 |
| 17 | tRNA (rat liver transfer RNA) | | | >1000 |
| 18 | perfectly matched "ds mir122a"<br>with a 3' poly A tail (1-50 As) | 5' pUGACUA--GAGACACAUUCAGCU 3' (SEQ ID NO:29) A(20-50) (SEQ ID NO:30)<br>3' polyA-AUACUGACACUGUUA(FAM-dT)CACAAp 5' | p▬▬▬▬▬▬▬<br>▬▬▬▬▬▬▬p | GEL SHIFT POSITIVE |

FIG. 8

| METHODS | ADVANTAGES | DISADVANTAGES |
|---|---|---|
| RADIOACTIVITY<br>P32 | • VERY SENSITIVE<br>• LOW BACKGROUND | • REGULATORY ISSUES<br>• LOW THROUGHPUT SCALE |
| FLUORESCENCE<br>FAM | • USER FRIENDLY METHOD<br>• PLATE 96 WELL:<br>POSSIBLE AUTOMATION | • METHOD DEVELOPMENT<br>(QUENCHING, SHIFTS)<br>• USE OF MEGNETIC BEADS |
| CHEMILUMINESCENCE<br>BIOTIN | • USER FRIENDLY METHOD<br>• PLATE 96 WELL:<br>POSSIBLE AUTOMATION | • MORE STEPS<br>• USE OF MAGNETIC BEADS |

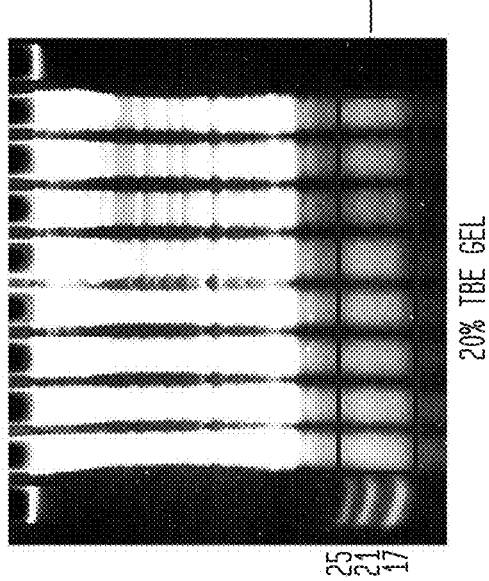

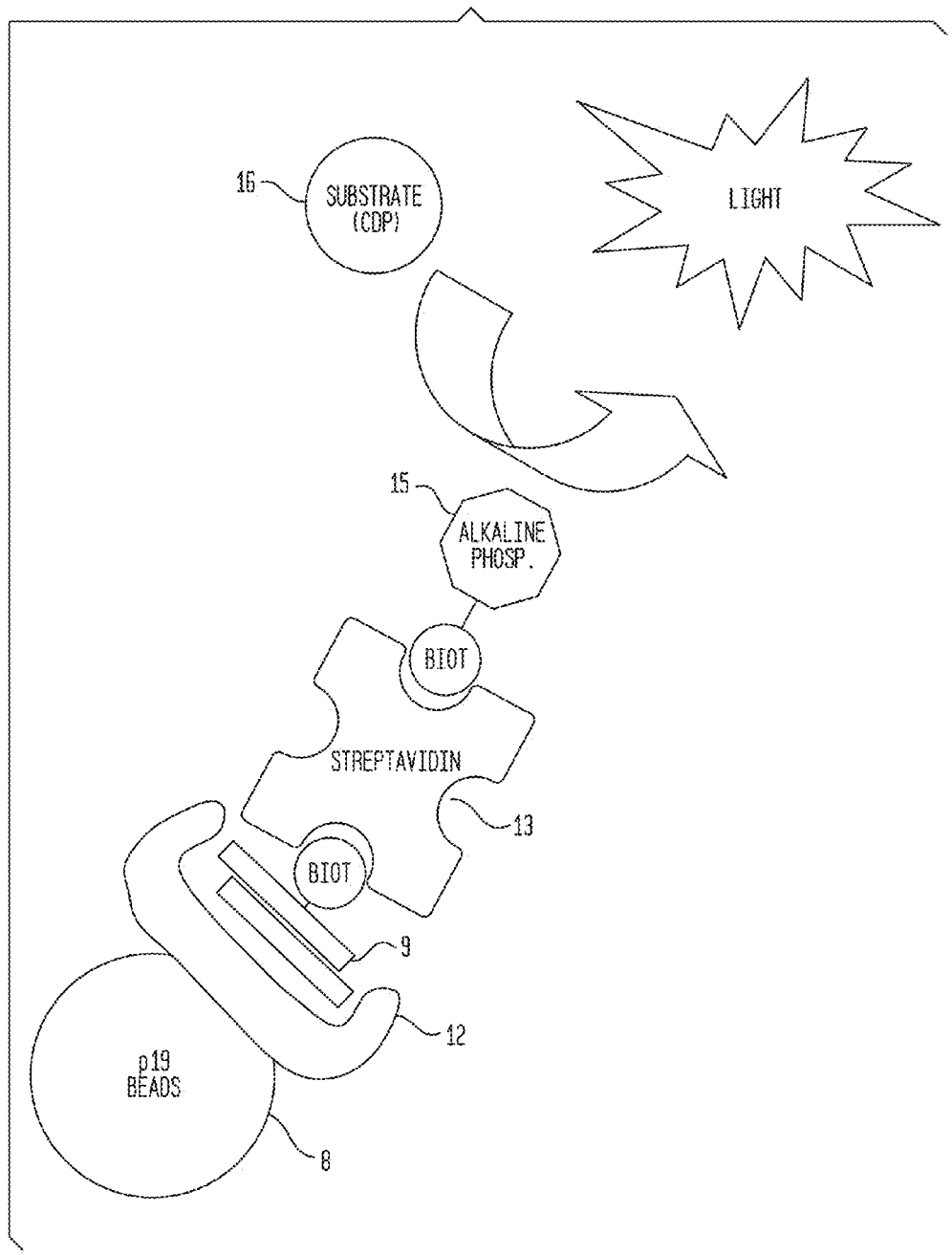

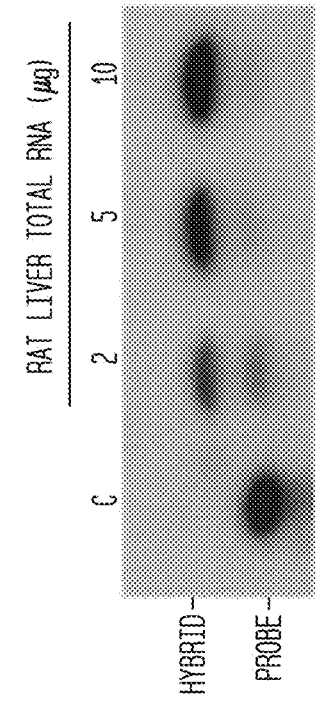
FIG. 17C
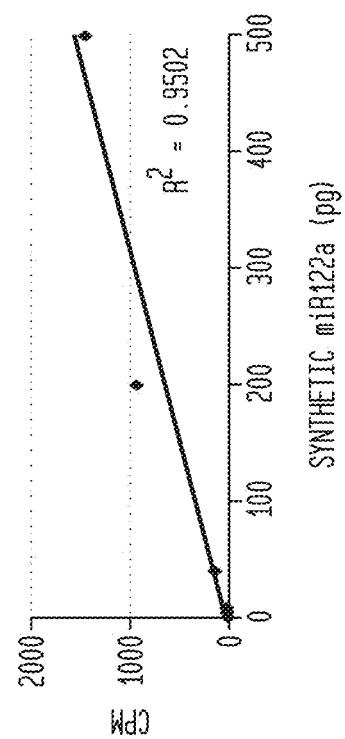
FIG. 17D
| RAT LIVER TOTAL RNA (μg) | miR122a (pg) | [miR122a] (pg/μg OF TOTAL RNA) |
|---|---|---|
| 2 | 127 | 63 |
| 5 | 215 | 43 |
| 10 | 383 | 38 |
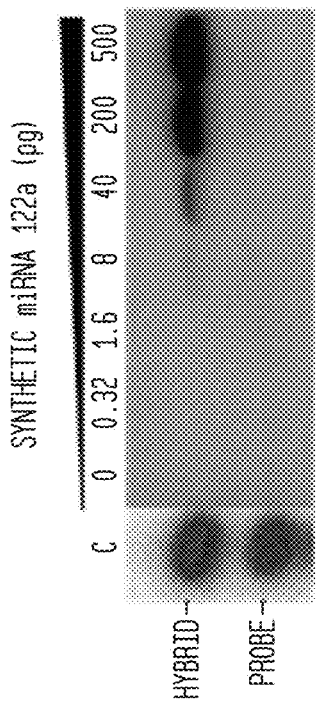
FIG. 17A
FIG. 17B

FIG. 19-1

```
      ATGAAAACTGAAGAAGGTAAACTGGTAATCTGGATTAACGGCGATAAAGGCTATAACGGT
  1   ------------------------------------------------------------  60
       M  K  T  E  E  G  K  L  V  I  W  I  N  G  D  K  G  Y  N  G

CTCGCTGAAGTCGGTAAGAAATTCGAGAAAGATACCGGAATTAAAGTCACCGTTGAGCAT
 61   ------------------------------------------------------------  120
       L  A  E  V  G  K  K  F  E  K  D  T  G  I  K  V  T  V  E  H

CCGGATAAACTGGAAGAGAAATTCCCACAGGTTGCGGCAACTGGCGATGGCCCTGACATT
121   ------------------------------------------------------------  180
       P  D  K  L  E  E  K  F  P  Q  V  A  A  T  G  D  G  P  D  I

ATCTTCTGGGCACACGACCGCTTTGGTGGCTACGCTCAATCTGGCCTGTTGGCTGAAATC
181   ------------------------------------------------------------  240
       I  F  W  A  H  D  R  F  G  G  Y  A  Q  S  G  L  L  A  E  I

ACCCCGGACAAAGCGTTCCAGGACAAGCTGTATCCGTTTACCTGGGATGCCGTACGTTAC
241   ------------------------------------------------------------  300
       T  P  D  K  A  F  Q  D  K  L  Y  P  F  T  W  D  A  V  R  Y

AACGGCAAGCTGATTGCTTACCCGATCGCTGTTGAAGCGTTATCGCTGATTTATAACAAA
301   ------------------------------------------------------------  360
       N  G  K  L  I  A  Y  P  I  A  V  E  A  L  S  L  I  Y  N  K

GATCTGCTGCCGAACCCGCCAAAAACCTGGGAAGAGATCCCGGCGCTGGATAAAGAACTG
361   ------------------------------------------------------------  420
       D  L  L  P  N  P  P  K  T  W  E  E  I  P  A  L  D  K  E  L

AAAGCGAAAGGTAAGAGCGCGCTGATGTTCAACCTGCAAGAACCGTACTTCACCTGGCCG
421   ------------------------------------------------------------  480
       K  A  K  G  K  S  A  L  M  F  N  L  Q  E  P  Y  F  T  W  P

CTGATTGCTGCTGACGGGGGTTATGCGTTCAAGTATGAAAACGGCAAGTACGACATTAAA
481   ------------------------------------------------------------  540
       L  I  A  A  D  G  G  Y  A  F  K  Y  E  N  G  K  Y  D  I  K

GACGTGGGCGTGGATAACGCTGGCGCGAAAGCGGGTCTGACCTTCCTGGTTGACCTGATT
541   ------------------------------------------------------------  600
       D  V  G  V  D  N  A  G  A  K  A  G  L  T  F  L  V  D  L  I

AAAAACAAACACATGAATGCAGACACCGATTACTCCATCGCAGAAGCTGCCTTTAATAAA
601   ------------------------------------------------------------  660
       K  N  K  H  M  N  A  D  T  D  Y  S  I  A  E  A  A  F  N  K

GGCGAAACAGCGATGACCATCAACGGCCCGTGGGCATGGTCCAACATCGACACCAGCAAA
661   ------------------------------------------------------------  720
       G  E  T  A  M  T  I  N  G  P  W  A  W  S  N  I  D  T  S  K

GTGAATTATGGTGTAACGGTACTGCCGACCTTCAAGGGTCAACCATCCAAACCGTTCGTT
721   ------------------------------------------------------------  780
       V  N  Y  G  V  T  V  L  P  T  F  K  G  Q  P  S  K  P  F  V

GGCGTGCTGAGCGCAGGTATTAACGCCGCCAGTCCGAACAAAGAGCTGGCAAAAGAGTTC
781   ------------------------------------------------------------  840
       G  V  L  S  A  G  I  N  A  A  S  P  N  K  E  L  A  K  E  F

CTCGAAAACTATCTGCTGACTGATGAAGGTCTGGAAGCGGTTAATAAAGACAAACCGCTG
841   ------------------------------------------------------------  900
       L  E  N  Y  L  L  T  D  E  G  L  E  A  V  N  K  D  K  P  L

GGTGCCGTAGCGCTGAAGTCTTACGAGGAAGAGTTGGCGAAAGATCCACGTATTGCCGCC
901   ------------------------------------------------------------  960
       G  A  V  A  L  K  S  Y  E  E  E  L  A  K  D  P  R  I  A  A

ACTATGGAAAACGCCCAGAAAGGTGAAATCATGCCGAACATCCCGCAGATGTCCGCTTTC
961   ------------------------------------------------------------ 1020
       T  M  E  N  A  Q  K  G  E  I  M  P  N  I  P  Q  M  S  A  F
```

FIG. 19-2

```
     TGGTATGCCGTGCGTACTGCGGTGATCAACGCCGCCAGCGGTCGTCAGACTGTCGATGAA
1021 ------------------------------------------------------------ 1080
      W  Y  A  V  R  T  A  V  I  N  A  A  S  G  R  Q  T  V  D  E

GCCCTGAAAGACGCGCAGACTAATTCGAGCTCGAACAACAACAACAATAACAATAACAAC
1081 ------------------------------------------------------------ 1140
      A  L  K  D  A  Q  T  N  S  S  S  N  N  N  N  N  N  N  N  N

AACCTCGGGCCGGGTGCGGCACACTACGTAGAATTCGGATCCATGGAACGAGCTATACAA
1141 ------------------------------------------------------------ 1200
      N  L  G  P  G  A  A  H  Y  V  E  F  G  S  M  E  R  A  I  Q

GGAAACGACACTAGGGAACAAGCTAACGGTGAACGTTGGGATGGAGGATCAGGAGGTATC
1201 ------------------------------------------------------------ 1260
      G  N  D  T  R  E  Q  A  N  G  E  R  W  D  G  G  S  G  G  I

ACTTCTCCCTTCAAACTTCCTGACGAAAGTCCGAGTTGGACTGAGTGGCGGCTATATAAC
1261 ------------------------------------------------------------ 1320
      T  S  P  F  K  L  P  D  E  S  P  S  W  T  E  W  R  L  Y  N

GATGAGACGAATTCGAATCAAGATAATCCCCTTGGTTTCAAGGAAAGCTGGGGTTTCGGG
1321 ------------------------------------------------------------ 1380
      D  E  T  N  S  N  Q  D  N  P  L  G  F  K  E  S  W  G  F  G

AAAGTTGTATTTAAGAGATATCTCAGATACGACAGGACGGAAGCTTCACTGCACAGAGTC
1381 ------------------------------------------------------------ 1440
      K  V  V  F  K  R  Y  L  R  Y  D  R  T  E  A  S  L  H  R  V

CTTGGATCTTGGACGGGAGATTCGGTTAACTATGCAGCATCTCGATTTCTCGGTGCCAAC
1441 ------------------------------------------------------------ 1500
      L  G  S  W  T  G  D  S  V  N  Y  A  A  S  R  F  L  G  A  N

CAGGTCGGATGTACCTATAGTATTCGGTTTCGAGGAGTTAGTGTCACCATTTCTGGAGGG
1501 ------------------------------------------------------------ 1560
      Q  V  G  C  T  Y  S  I  R  F  R  G  V  S  V  T  I  S  G  G

TCGAGAACTCTTCAGCATCTCTGTGAGATGGCAATTCGGTCTAAGCAAGAACTGTTACAG
1561 ------------------------------------------------------------ 1620
      S  R  T  L  Q  H  L  C  E  M  A  I  R  S  K  Q  E  L  L  Q

CTTACCCCAGTCGAAGTGGAAAGTAATGTATCAAGAGGATGCCCTGAAGGTATTGAAACC
1621 ------------------------------------------------------------ 1680
      L  T  P  V  E  V  E  S  N  V  S  R  G  C  P  E  G  I  E  T

TTCAAGAAAGAAAGCGAGGGATCCTCTAGAGTCGACCTGCAGACGACAAATCCTGGTGTA
1681 ------------------------------------------------------------ 1740
      F  K  K  E  S  E  G  S  S  R  V  D  L  Q  T  T  N  P  G  V

TCCGCTTGGCAGGTCAACACAGCTTATACTGCGGGACAATTGGTCACATATAACGGCAAG
1741 ------------------------------------------------------------ 1800
      S  A  W  Q  V  N  T  A  Y  T  A  G  Q  L  V  T  Y  N  G  K

ACGTATAAATGTTTGCAGCCCCACACCTCCTTGGCAGGATGGGAACCATCCAACGTTCCT
1801 ------------------------------------------------------------ 1860
      T  Y  K  C  L  Q  P  H  T  S  L  A  G  W  E  P  S  N  V  P

GCCTTGTGGCAGCTTCAATGA       (SEQ ID NO:32)
1861 ---------------------- 1881
      A  L  W  Q  L  *          (SEQ ID NO:33)
```

METHODS AND COMPOSITIONS FOR DETECTION AND ENRICHMENT OF TARGET SMALL RNAS

CROSS REFERENCE

This application is a divisional application of U.S. Ser. No. 12/738,580 filed Apr. 16, 2010, which is a §371 application of international application number PCT/US08/081,520 filed on Oct. 29, 2008, which claims priority from U.S. provisional application Ser. No. 60/983,503 filed on Oct. 29, 2007, herein incorporated by reference.

BACKGROUND

Existing methods for detection of small RNAs such as small interfering RNAs (siRNAs) and micro RNAs (miRNAs) often involve multiple steps: for example, immobilizing RNA on a filter (Northern blot), hybridization with a specific probe if the small RNA is a single-stranded miRNA, washing steps to remove the probe, and exposure of the filter to a film. Alternatively, small single-stranded RNAs (ssRNAs) such as micro RNAs (miRNAs) can be detected using solution hybridization of a probe to the miRNAs, RNAse treatment and gel electrophoresis to analyze the miRNA/probe product. Detection of miRNA using a DNA array requires fluorescent-labeling of total RNA. Labeling of samples adds complexity and variability to the results. Methods that require DNA amplification are sensitive but need corrections related to efficiency of amplification. These methods are not appropriate for rapid diagnostics or high throughput screening because of the multiple steps involved in the analysis.

Evidence is accumulating that small RNAs such as miRNAs are involved in human disease such as neurological diseases, cardiomyopathies, and cancers (Alvarez-Garcia et al. Development 132:4653-4662 (2005)). Patterns of altered miRNA expression in tissue biopsies may serve as diagnostic markers for these diseases. For example, the use of a reliable quantitative method for detecting the differential expression of certain miRNAs in various tumors would be valuable for diagnosis and treatment of cancer.

SUMMARY

In an embodiment of the invention, a recombinant protein is provided having at least 90% sequence homology to SEQ ID NO:33, and being capable of binding a small double-stranded RNA (dsRNA). The recombinant protein may be additionally labeled by means of a fluorescent label, a radioactive label, a chemiluminescent label, a protein label or a small molecule label. In another embodiment of the invention, a DNA encoding the recombinant protein and a vector for expressing the recombinant protein in a host cell are provided.

In a further embodiment of the invention, a method is provided that includes mixing a target RNA with a p19 fusion protein capable of binding small dsRNA, wherein either the p19 fusion protein or the target RNA is labeled, the label being (i) directly linked to the protein or RNA, or (ii) indirectly linked by means of a molecule capable of binding to the p19 fusion protein or the target RNA. The method further includes immobilizing the p19 fusion protein bound to the target RNA on a matrix for detecting the target RNA. The detectable label is exemplified by a member of the group consisting of a fluorescent label, a radioactive label, a chemiluminescent label, a protein label and a small molecule label.

The target RNA may be an ssRNA having a size in the range of 18 nucleotides to 24 nucleotides where the ssRNA hybridizes to a complementary polynucleotide probe to form a double-stranded hybrid polynucleotide for binding to the p19 fusion protein. The complementary polynucleotide probe may extend at the 3' end beyond the target RNA.

The polynucleotide probe may be an RNA, a DNA or a locked nucleic acid. The target RNA may be a single-stranded molecule such as a miRNA. The target RNA may be a double-stranded RNA such as an siRNA.

In an embodiment of the invention, the p19 fusion protein is immobilized prior to binding the target RNA. Alternatively, the target RNA may be immobilized prior to binding the p19 fusion protein. Alternatively, the p19 fusion protein may be bound to the target RNA in solution and the p19 fusion protein dsRNA complex immobilized on a matrix.

In embodiments of the invention, the matrix is a bead which may be coated with a carbohydrate or other ligand to which the p19 fusion protein binds. The bead may be magnetic. The bead may be colored or fluorescent in a manner that differs from the label on the p19 fusion protein or polynucleotide probe.

In an embodiment of the invention, immobilization of target RNA provides a diagnostic test for an abnormal condition in a cell in which the target RNA is isolated from total RNA obtained from the cell.

In an embodiment of the invention, a method is provided for detecting a target RNA in a mixture of RNAs, such that if the target RNA is (i) single-stranded, then a complementary polynucleotide probe is added to the mixture for forming a dsRNA and allows the dsRNA to bind to a p19 fusion protein; or (ii) double-stranded, in which case dsRNA binds directly to the p19 fusion protein.

In either case, one of the complementary polynucleotide probes or the p19 fusion protein is associated or linked to a label selected from a fluorescent label, a radioactive label, a chemiluminescent label, a protein label and a small molecule label.

In a further embodiment of the detection method, p19 fusion protein can be immobilized on a matrix for binding small dsRNA and removing unbound RNA. Alternatively, small dsRNAs can be immobilized on the matrix either by hybridizing a target ssRNA to a matrix bound polynucleotide probe or by directly binding the target dsRNA. In this case, the p19 fusion protein is preferably labeled.

In a further embodiment of the invention, a kit is provided that contains the recombinant p19 fusion protein described above, instructions for detecting a small RNA, and optionally a matrix for binding p19 fusion protein or a polynucleotide probe. The p19 fusion protein may be bound to a matrix in the kit. Alternatively, a polynucleotide probe may be bound to the matrix, in which case, the kit may additionally contain a labeled unbound p19 fusion protein.

If a matrix is included in the kit, it may be a bead, for example, a colored or fluorescent bead. The bead may be coated with a carbohydrate for binding the p19 fusion protein. The bead may be magnetic.

BRIEF DESCRIPTION OF THE DRAWINGS

FIG. 2A shows a cartoon of a fusion protein consisting of a maltose-binding protein (MBP) fused to p19 which is fused to a chitin-binding domain (CBD).

FIG. 2B shows a gel containing the p19 fusion protein. The figure demonstrates that this protein can be made in large quantities.

FIG. 2C shows the crystal structure of the p19 fusion protein bound to dsRNA. The view is looking down the center of the RNA helix.

FIG. 4A shows that 10 ng, 20 ng, 30 ng and 40 ng of dsRNA can be bound to chitin magnetic beads that contain 3 μg of the p19 fusion protein. The fusion protein is attached to the beads via the CBD. When treated with SDS, the dsRNA is released from the beads and can be detected on the ethidium stained gel.

FIG. 4B shows that a small amount of dsRNA of 21 nucleotides can be purified from a large excess of cytoplasmic RNA using p19 fusion protein. Chitin magnetic beads with 5 μg of the bound p19 fusion protein were mixed with 27.5 μg of total rat liver RNA and 5 ng of 21-mer dsRNA.

Lane 1 shows target dsRNA prior to mixing with non-target RNA.

Lane 2 shows the RNA that did not bind to the p19 fusion protein chitin magnetic beads.

Lane 3 shows 20 μl aliquot of the first 600 μl wash of the p19 fusion protein chitin magnetic beads.

Lane 4 shows a 20 μl aliquot of the sixth 600 μl wash of the p19 fusion protein chitin magnetic beads.

Lane 5 shows the dsRNA eluted from the beads. The top staining band is material trapped in the well.

Lane 6 contains a 17-mer, 21-mer and 25-mer dsRNA marker.

FIGS. 5A and 5B show a competitive gel shift assay to measure the relative affinity of RNA and DNA to the p19 fusion protein.

FIG. 5A shows binding of radiolabeled dsRNA (21 nt) to p19 fusion protein in the presence of increasing amounts of the same unlabeled dsRNA (21 nt). Each reaction contained 16 μg of p19 fusion protein and 1 ng of radioactive dsRNA.

FIG. 5B shows binding of radiolabeled dsRNA (21 nt) to fusion protein in the presence of increasing amounts of unlabeled double-stranded DNA (dsDNA) (21 nt).

FIG. 5C shows binding of radiolabeled dsRNA (21 nt) to p19 fusion protein in the presence of increasing amounts of unlabeled ribosomal RNA.

FIG. 5D shows binding of radiolabeled dsRNA (21 nt) to p19 fusion protein in the presence of increasing amounts of unlabeled ssRNA (21 nt).

Figure 6B:
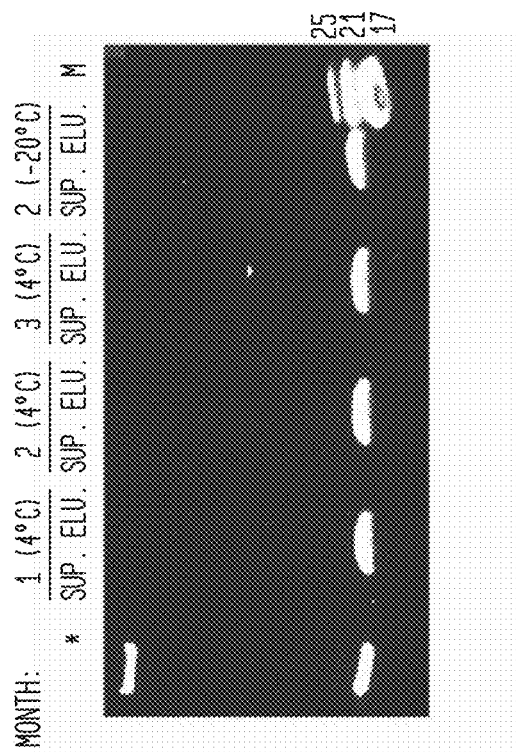
Figure 6A:
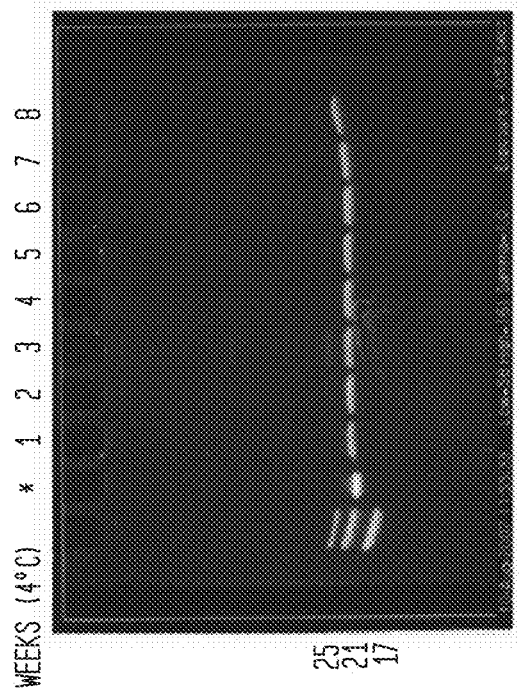

FIGS. 6A-6B show the results of eluting 20 ng of 21 nt dsRNA from 20 μl p19 fusion protein precoated beads (containing 3 μg p19 fusion protein).

FIG. 6A shows that p19 fusion protein is stable when stored at 4° C. for at least 8 weeks such that the 21 nt RNA can be released after the specified time.

FIG. 6B shows that 21-mer dsRNA is stable when bound to p19 fusion protein stored at 4° C. or −20° C. The absence of RNA in the supernatent shows efficient binding of RNA. The elution demonstrates quantitative recovery of dsRNA from p19 fusion protein beads stored for different times and temperatures.

FIG. 7 shows the relative binding affinities of p19 fusion protein to various RNA and DNA substrates. The binding of a labeled siRNA to MBP-p19-CBD in the presence of increasing concentrations of nucleic acids described in column 1 was measured by a gel mobility shift assay. In each competitive assay, a control was included in which 50% reduction in binding of the radiolabeled 21 mer siRNA was observed in the presence of unlabeled 21 mer siRNA. This was assigned a value of one. The identity of the polynucleotide, its sequence, its structure and its relative binding affinity to MBP-p19-CBD are listed. The gaps in the structure of the microRNAs in 13, 14 and 15 denote mismatched base pairs.

FIG. 8 describes various approaches to labeling RNA. Radioactive labeling is very sensitive and gives low background but is not suitable for high throughput analysis and also has regulatory issues. Fluorescence and chemiluminescence labeling are both user friendly labeling methods and can be used in a 96 well format with or without magnetic beads and are scaleable and can be automated.

Figure 9:
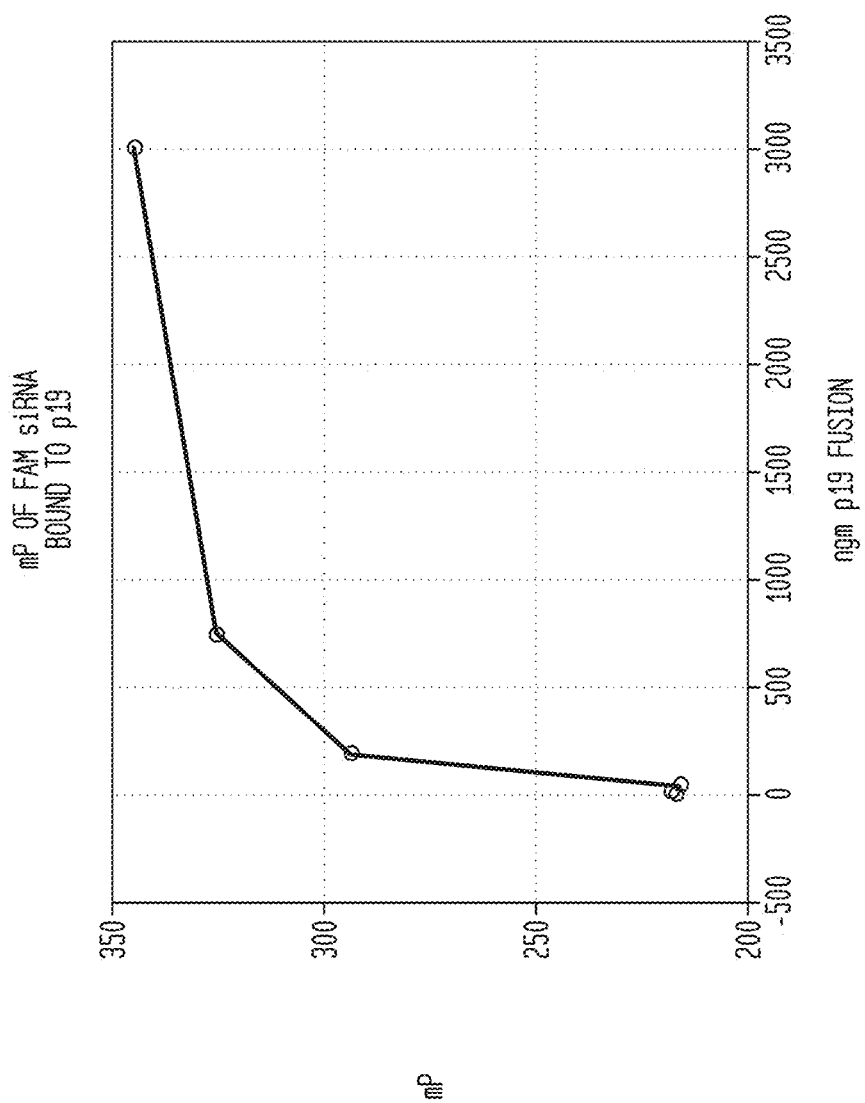

FIG. 9 shows how MBP-p19-CBD (measured in ng) when bound to fluorescent dsRNA increases fluorescence polarization which can be quantitatively measured (mP). Fluorescence polarization is defined by the following equation: $P=(V-H)/(V+H)$ where P equals polarization, V equals the vertical component of the emitted light, and H equals the horizontal component of the emitted light of a fluorophore when excited by vertical plan polarized light. The term mP stands for $1/1000$ of the polarization P. It is not dependent upon concentration (Lundblad et al. *Mol. Endocrinol.* 10:607-612 (1996)).

FIGS. 10A-10B show how the p19 fusion protein can be used for discovery of novel endogenous siRNAs.

FIG. 10A shows the results of loading 350 μg of total unc-22 RNA extracted from *C. elegans* onto a 20% acrylamide TBE gel. Extraction of RNA from the gel in the 15 to 30 base pair range yields 6.1 μg of small RNA.

FIG. 10B shows the results from binding the gel purified small RNA to the p19 fusion protein chitin magnetic beads, washing the beads and then eluting the RNA. The mobility of the eluted RNA is indicated by an arrow at the right of the figure.

Figure 11:
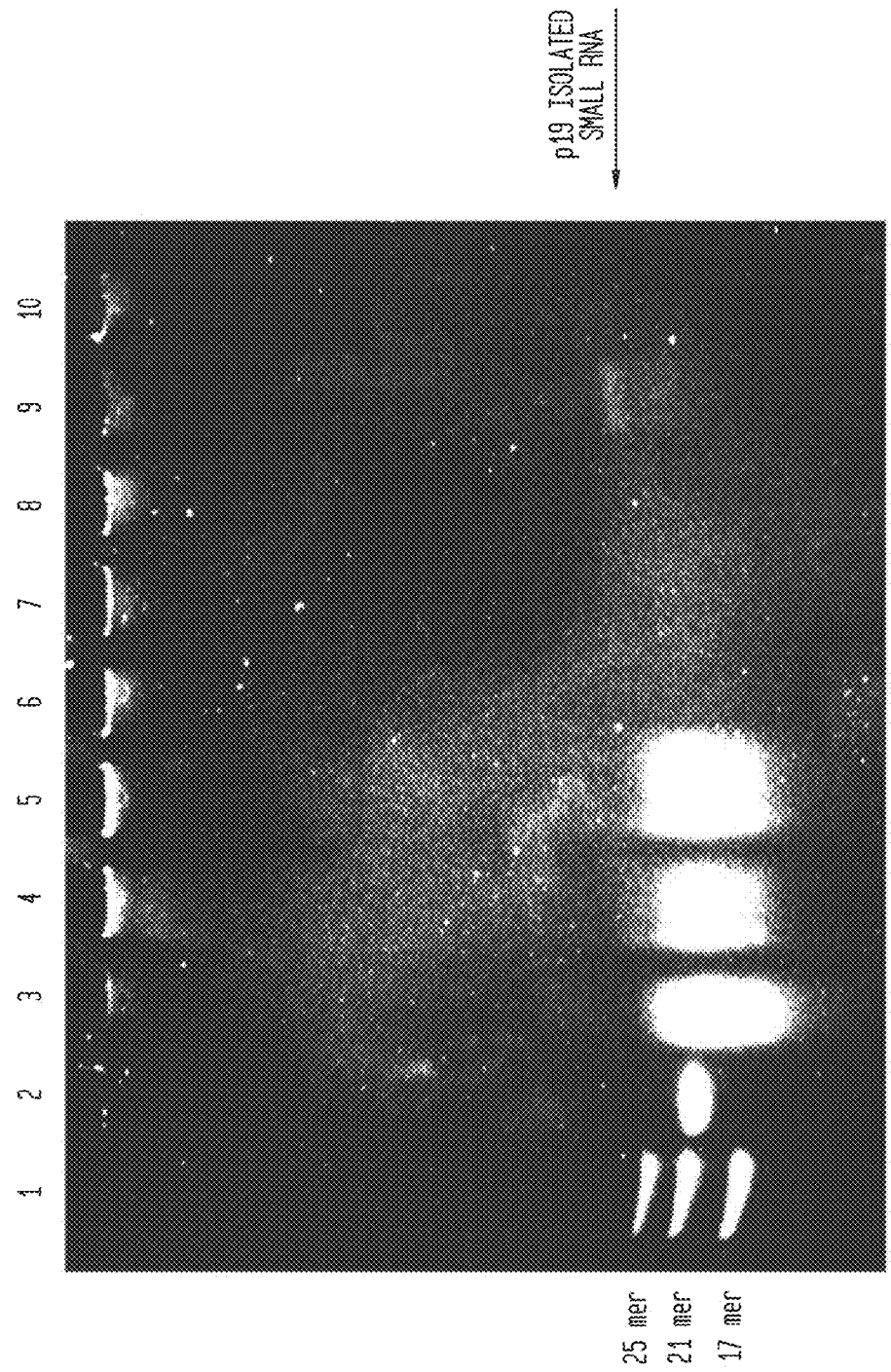

FIG. 11 shows the isolation of endogenous siRNA from a filiarial parasite *D. immitis* using p19 fusion protein chitin magnetic beads. 50,000 fold enrichment was obtained. The mobility of the eluted RNA, in lane 9, is indicated by an arrow.

Lane 1 is double-stranded siRNA marker.
Lane 2 is 10 ng of a 21 mer dsRNA.
Lane 3 is gel purified *D. immitis* small RNA.
Lane 4 is gel purified RNA plus p19 fusion protein.
Lane 5 is RNA not bound to chitin magnetic beads with p19 fusion protein.
Lane 6 is the first wash of the p19 chitin magnetic beads.
Lane 7 is the result of wash 2.
Lane 8 is the result of wash 3.

Lane 9 is the first elution from the beads.
Lane 10 is the second elution from the beads.

Figure 12:
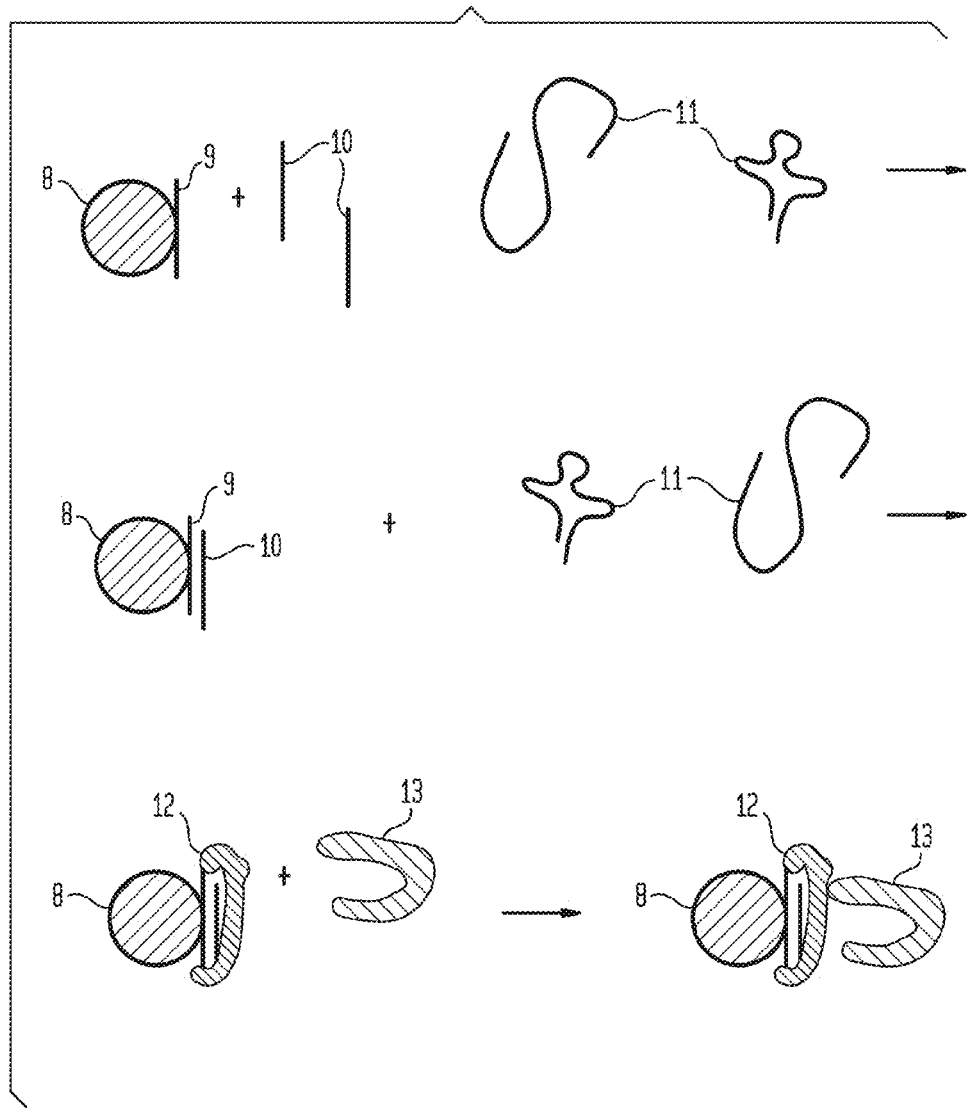

FIG. 12 shows a protocol for detecting dsRNA using biotin-labeled p19 fusion protein. A polynucleotide probe (9) is covalently linked to beads (8). Small ssRNAs (tRNAs, rRNAs etc.) (10) hybridize to the polynucleotide probe (9) to form a stable RNA hybrid on the bead (8). A biotin-labeled p19 fusion protein (12) binds to RNA hybrids on the beads (8). The p19 fusion protein can be labeled using biotin, which can bind tightly to streptavidin (13). The streptavidin can be detected by linkage via a second biotin molecule to an enzyme, like alkaline phosphatase or peroxidase, or by means of a fluorescent-labeled protein. Substrates for the enzyme will give a colored or fluorescent product that can be detected with a laser. The beads to which p19 fusion protein attaches can be identified with a laser which detects the bar code signature of dyes. The amount of miRNA bound to a specific bead can be measured by the amount of p19 fusion protein bound to the beads.

Figure 13:
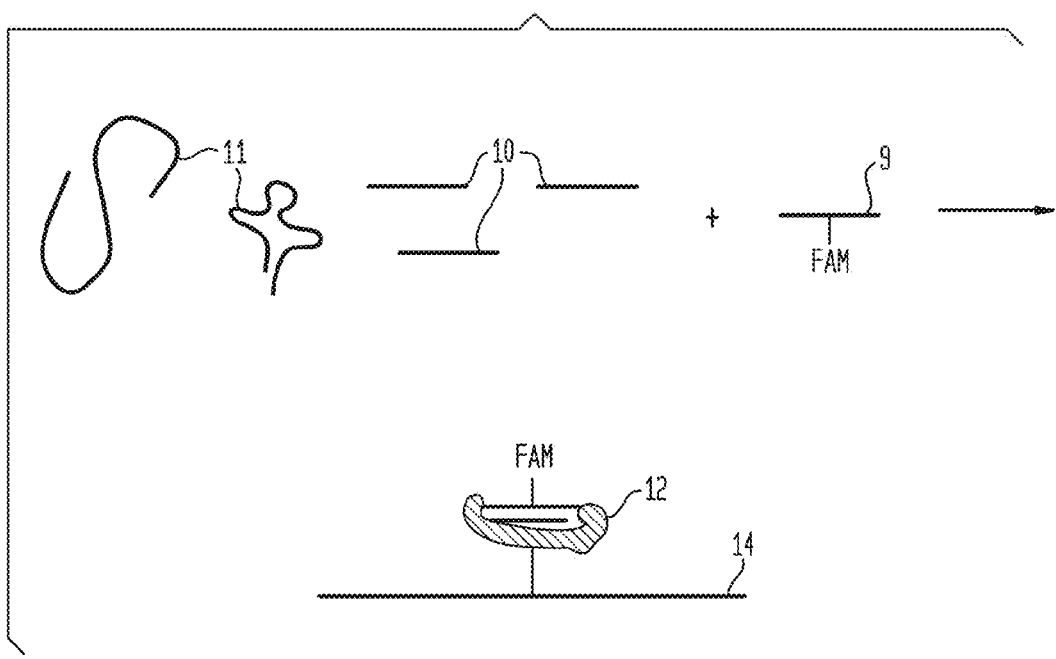

FIG. 13 shows p19 fusion protein capture of dsRNA hybrid and detection with a miRNA specific probe. An ssRNA polynucleotide (9) labeled with (5-[(N-(3'-diphenylphosphinyl-4'-methoxycarbonyl)phenylcarbonyl)aminoacetamido]fluorescein (FAM) binds specifically to miRNA (10) in a background of total RNA including tRNA, rRNA and mRNA (11) to form a dsRNA that binds to a p19 fusion protein (12) which is attached to a solid support, like an ELISA plate (14) or a bead for detection.

Figure 14:
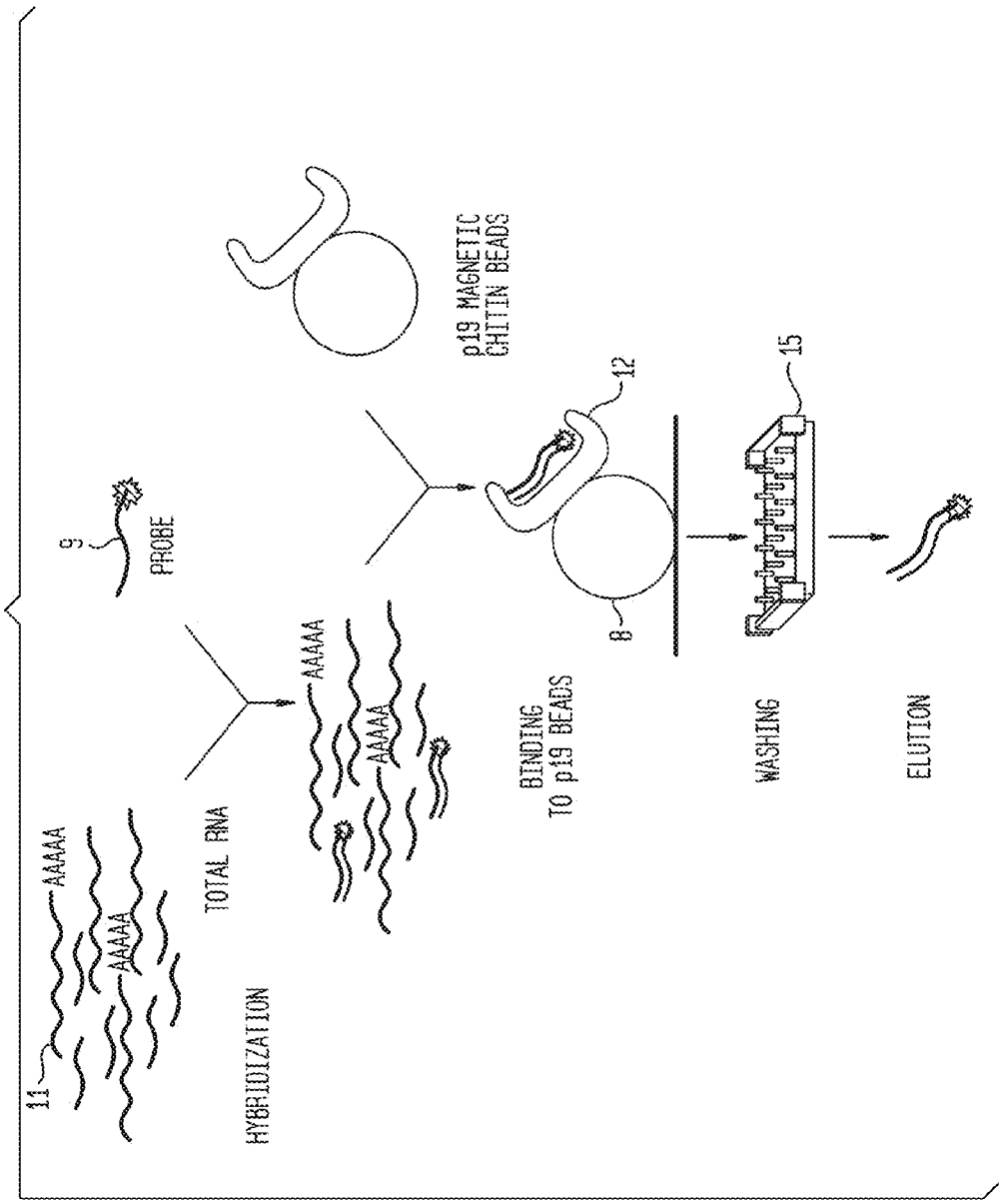

FIG. 14 shows a p19 fusion protein-based miRNA detection method. Total cellular RNA, which includes miRNA, rRNA and mRNA (11), is hybridized to a specific probe complementary to a miRNA (9). The double-stranded miRNA/RNA probe is then selectively and tightly bound to p19 fusion protein (12) chitin magnetic chitin beads (8). The unbound probe can be removed rapidly by washing the p19 fusion protein beads and then isolating them with the aid of a magnetic rack (15). The dsRNA is then eluted from the beads in the presence of a protein denaturing agent.

Figure 15B:
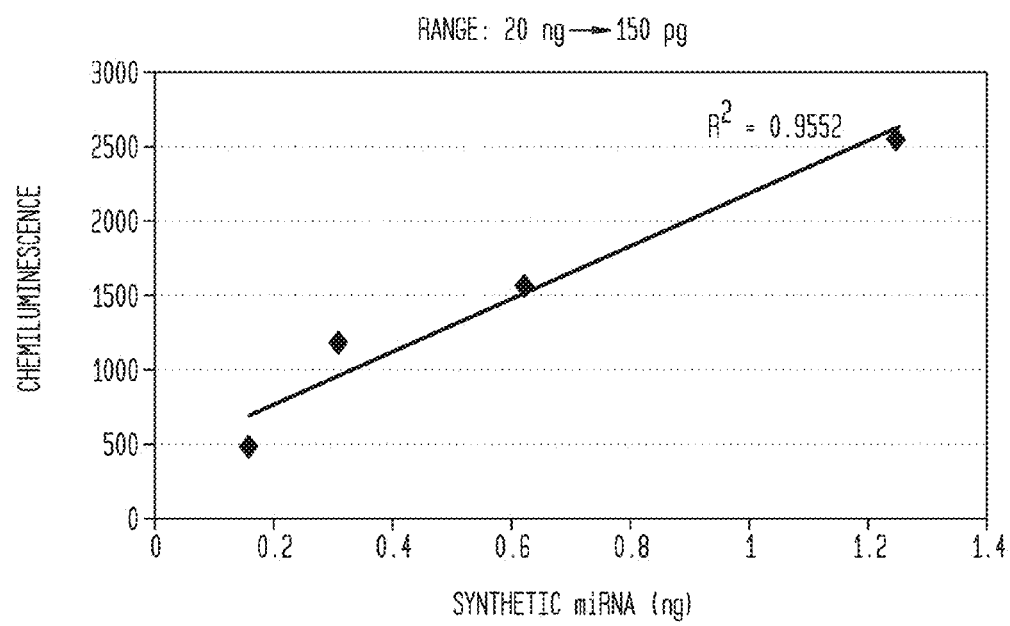

FIGS. 15A and 15B show a diagnostic test for miRNAs.

FIG. 15A shows p19 fusion protein (12) attached to a bead (8) and binding dsRNA where a single strand of the duplex is labeled with biotin (9). Streptavidin (13) is bound to the biotin and with the help of a suitable enzyme label (15) and a substrate (16), a chemiluminescent or fluorescent reaction can be initiated.

FIG. 15B shows a standard curve assay for quantifying the results from the detection method described in FIG. 15A. The biotin-labeled RNA probe is linked, via a streptavidin bridge, to alkaline phosphatase. The enzyme is detected using the substrate CDP-Star, #N7001S from New England Biolabs (NEB, Ipswich, Mass.), which generates light.

Figure 16:
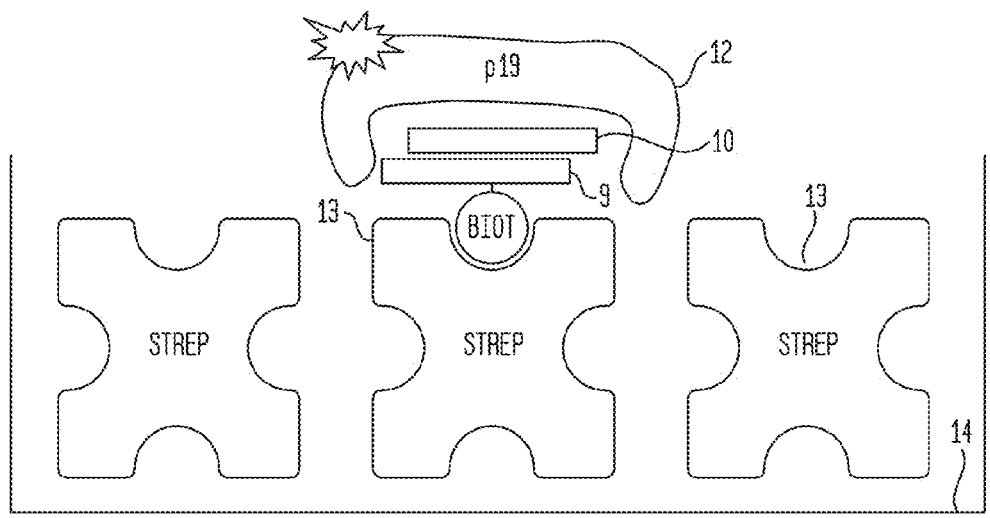

FIG. 16 shows a biotin-labeled ssRNA (9) immobilized on a streptavidin (13) coated solid substrate (14). Target miRNA (10) is hybridized to the immobilized polynucleotide (9). The dsRNA is subsequently recognized and bound by a labeled p19 fusion protein (12) for detection.

FIGS. 17A-17D show the quantitative measurement of the liver specific miRNA (miRNA122a) from rat liver total RNA.

FIG. 17A shows a non-denaturing gel with increasing amounts of synthetic miRNA122a in picograms (pg), hybridized to 1 ng of a radioactive RNA probe complementary to miR-122a. The dsRNA is bound to p19 fusion protein chitin magnetic beads, washed, eluted and analyzed on a 20% non-denaturing acrylamide gel. The radioactivity is associated with the miRNA/RNA probe.

FIG. 17B shows a standard curve for miR122 that was calculated from radioactivity eluted from the p19 fusion protein beads.

FIG. 17C shows a non-denaturing gel of miRNA/RNA probe eluted from p19 fusion protein beads using a miR122 specific probe and different amounts of rat liver RNA.

FIG. 17D gives the results for 2, 5 and 10 µg of rat liver total RNA containing between 38 and 68 µg of miRNA122a/µg of total RNA.

Figure 18:
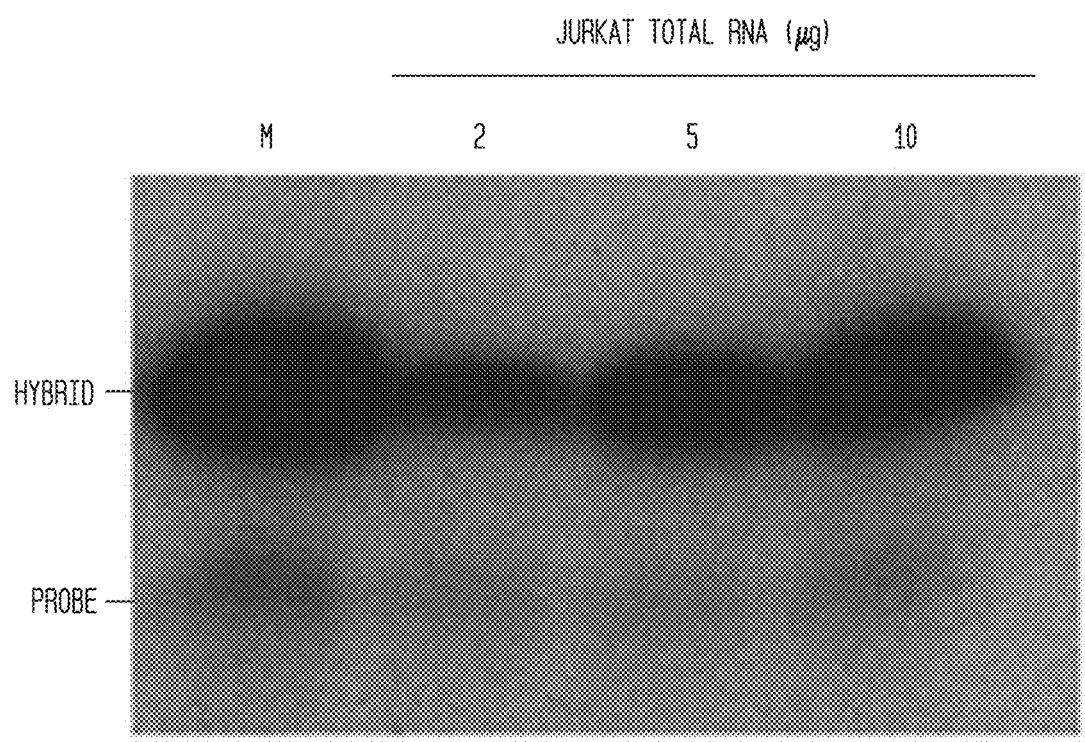

FIG. 18 shows detection of Let-7 miRNA in total JURKAT cell RNA using an autoradiograph of an acrylamide gel in which the labeled RNA corresponds to the miRNA/RNA probe hybrid, which is shown to increase according to the total RNA. A radioactive RNA probe complementary to Let-7 was hybridized to different amounts of JURKAT cell RNA, bound to p19 fusion protein magnetic beads, washed and eluted. Lanes 2-4 show 2 µg, 5 µg and 10 µg of total JURKAT RNA respectively.

FIG. 19 shows the DNA and amino acid sequences (SEQ ID NOS:32 and 33) for CBD-p19-MBP where MBP corresponds with amino acid 1 to 394 and nucleotide 1 to 1183, p19 corresponds with amino acid 395 to 565 and nucleotide 1184 to 1698, a polylinker corresponds with amino acid 566 to 575 and nucleotide 1698 to 1726 and CBD corresponds with amino acid 576 to 626 and nucleotide 1727 to 1878.

DETAILED DESCRIPTION OF THE EMBODIMENTS

Existing methods for detection of small RNAs are often complex and require ligation and amplification or gel electrophoresis steps. A fusion protein is described here that can be used in a simplified, sensitive and quantitative assay to detect and/or isolate small RNAs.

The fusion protein described here is exemplified by a p19 fusion protein which binds a dsRNA regardless of the sequence but in a size-specific manner, is capable of being immobilized on a substrate, and can be readily purified.

RNAs of interest can be isolated from biological samples using the p19 fusion protein. This protein may also be used to detect specific endogenous RNAs of a specific size in physiological samples that contain a wide variety of RNAs normally associated with cells. The amounts of the RNAs of interest can be determined using quantitative assays (see for example, FIGS. 9, 15 and 17).

DEFINITIONS

The term "small" RNA as used here and in the claims refers to RNA fragments containing or capable of forming a double-stranded region of a size of greater than about 17 nucleotides and less than about 25 nucleotides, for example 21-23 nucleotides. The dsRNA may result from two complementary strands in a linear duplex or a single-stranded molecule that is folded to form a hairpin.

Where a small RNA is single-stranded, it can be hybridized to a complementary polynucleotide probe to create either a completely dsRNA molecule or RNA/DNA hybrid or a partial dsRNA. The RNA/RNA or RNA/DNA hybrids may include a single-stranded polynucleotide tail at one end of the polynucleotide probe that extends beyond the duplex region containing the target RNA.

Examples of small RNAs include miRNAs, siRNAs, repeats associated RNAs (rasiRNAs). rasiRNAs are found for example in *C. elegans* and may prevent migration of transposons.

The "p19 fusion protein" refers to a member of the p19 family of RNA binding proteins (Silhavy et al. *Embo J.* 21:3070-80 (2002)) fused to one or more additional proteins which surprisingly retains the binding properties of the native enzyme where the fusion protein binds small dsRNA in a sequence-unspecific but size-specific manner (see for example, FIGS. 2-6). The binding properties of the p19 fusion protein was determined for various substrates using competitive gel shift analysis. The results confirmed that the p19 fusion protein does not bind ssRNAs or dsDNA but does bind dsRNA in a size specific manner (FIG. 7).

P19 proteins are highly conserved in Tombus plant viruses. Related proteins have been isolated from many plant viruses such as Carnation Italian ringspot virus p19 (NP 612584), Tomato bushy stunt virus (CAC01278), Artichoke mottled crinkle virus (NP 039812), Lettuce necrotic stunt virus (CAC01267), Lisianthus necrosis virus (CAM98056), Grapevine Algerian necrosis virus (AAX76895), Cucumber necrosis virus (CAC01089), Pelargonium necrotic spot virus (NP 945118), Cucumber Bulgarian virus (AA033943), Maize necrotic streak virus (AAG21219), Pear latent virus (AAM49806), Grapevine Algerian latent virus (AAX76895), and Cymbidium ringspot virus (CAA33535) (accession numbers in parenthesis).

The p19 proteins described above includes a fusion to one or more proteins where at least one of the proteins has a size greater than 10 amino acids. Examples of proteins for fusion to p19 include carbohydrate-binding proteins exemplified by MBP, CBD and cellulose-binding domain; enzymes such as 06-alkylguanine-DNA alkyltransferase (U.S. Patent Applications 2006/0292651; 2006/0024775; 2004/0115130; 2007/0082336; 2007/0207532; 2007/0243568) or luciferase that are capable of responding to a substrate to produce fluorescence or a detectable color signal; enzyme substrates such as biotin; antibodies; and protein epitopes.

A "polynucleotide probe" refers to a ssDNA, ssRNA or a locked nucleic acid that may be synthetic and is complementary at least in part to the target RNA if the target RNA is single-stranded (Vester & Wengel *Biochemistry* 43(42):13233-41 (2004)). The probe may be labeled. Alternatively, the probe is not labeled and is used in an assay in which the p19 fusion protein is or becomes labeled during the assay.

Methods of Making p19 Fusion Proteins

Figure 1:
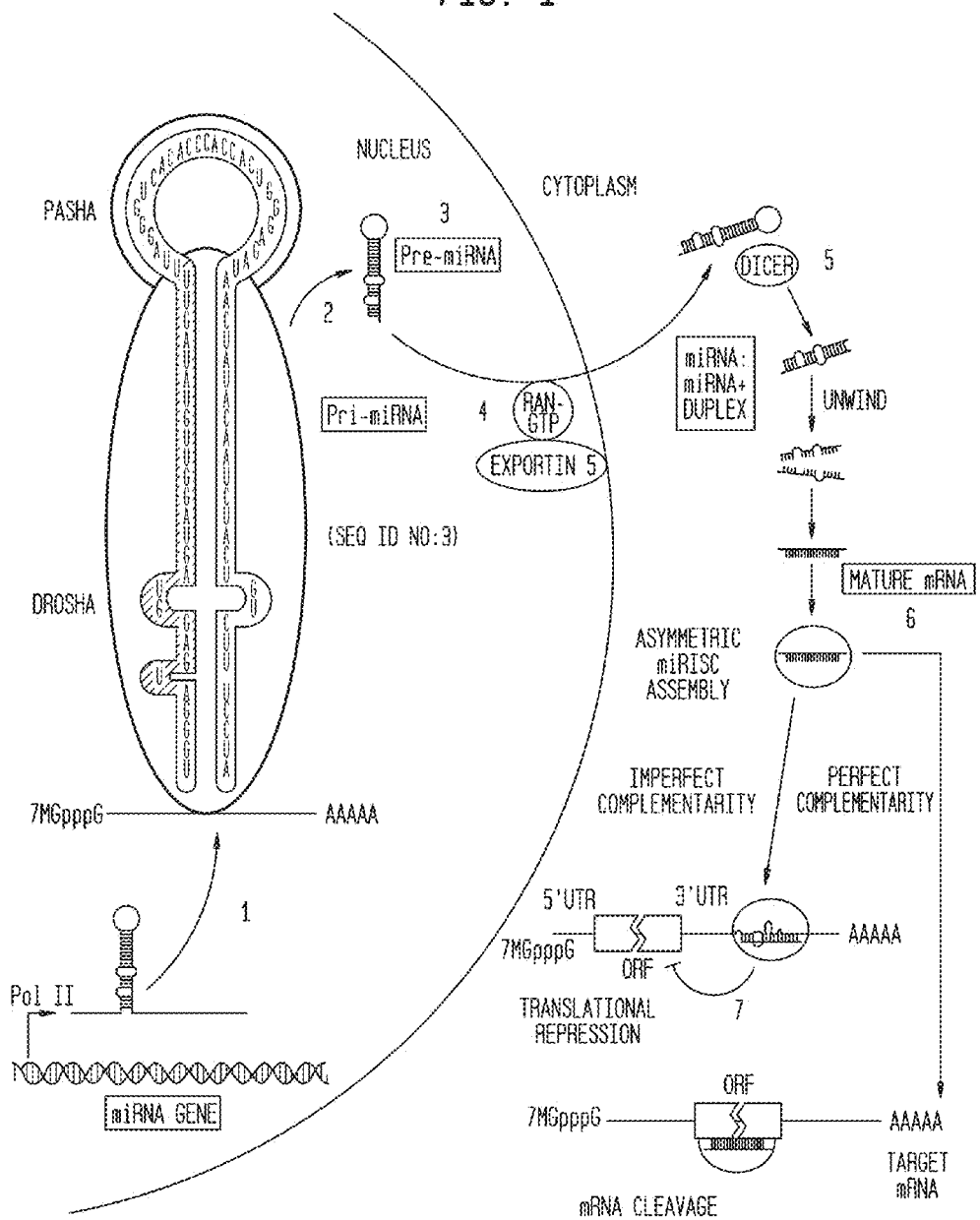
FIG. 1 shows a summary of the biogenesis of miRNAs (Esquela-Kerscher & Slack, Nature Reviews Cancer 6:259-269 (2006)). Transcription (1) of DNA results in the formation of a primary miRNA (pri-miRNA) (SEQ ID NO:3). This is a dsRNA hairpin structure that is cleaved by Drosha (2), a nuclear enzyme with RNase III domains to form a pre-miRNA (3). The cleaved hairpin is transported to the cytoplasm (4) by exportin 5. Secondary cleavage occurs with Dicer (5) to generate a dsRNA of about 20 to 22 bases in length. This RNA then enters the RNA-induced silencing complex where it is unwound to form ssRNA that hybridizes with the 3' untranslated region of the miRNA (6). The bound miRNA reduces protein expression either by blocking translation or causing cleavage of the miRNA (7).
Figure 2A:
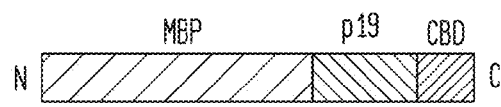
FIGS. 2A-2C show properties of the molecule used for discovery or detection of miRNA.
Figure 2B:
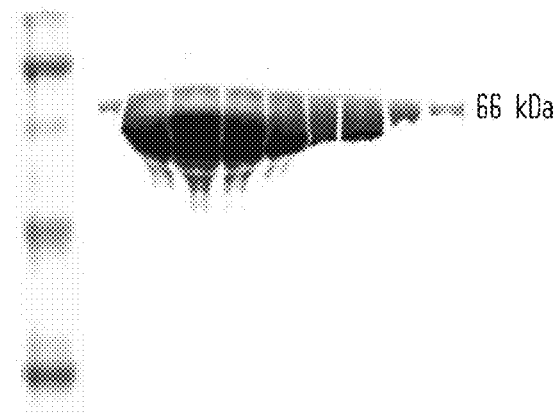
Figure 2C:
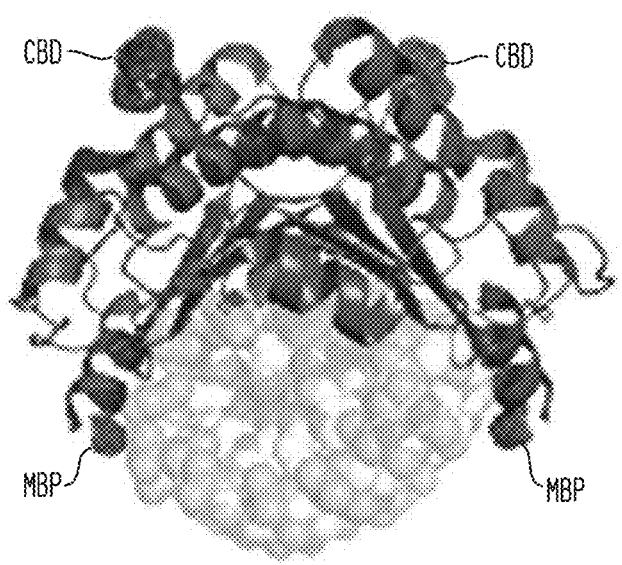

The formation of fusion proteins can be readily achieved using DNA vectors available in the art such as those described in the New England Biolabs (NEB, Ipswich, Mass.) catalog. Example 1 which is not intended to be limiting describes a method of making a p19 fusion protein from Carnation Italian ring spot virus in which the protein is fused at the amino end to an MBP, which permits purification of the protein, and at the carboxy end to the CBD, for tightly binding the magnetic chitin beads (FIG. 2).

Labeling the p19 Fusion Protein or Polynucleotide Probe

Labeling a target molecule may be achieved either directly or indirectly by labeling a molecule capable of binding the target molecule. These labels may be attached to a reagent polynucleotide probe for binding the target RNA, or to the p19 fusion protein. Any suitable label known in the art can be used such as a radioactive label (for example, $^{32}P$), a fluorescent label, a chromogenic label such as phycoerythrin, an enzyme label or a modified base for reacting with an enzyme (biotin-strepavidin).

Examples of methods of detection using fluorescent labels include FAM. Another method is Fluorescence Resonance Energy Transfer (FRET). This involves two different fluorescent molecules (or proteins), one for linking to the p19 fusion protein and the other for linking to the RNA probe. When the dsRNA binds to the p19 fusion protein, the two molecules are in close enough proximity for efficient energy transfer to generate a fluorescent signal. This method does not require removal of the unbound RNA probe and is therefore suitable for large scale screening. Another method is Fluorescent Polarization (FP) where the two subunits of the MBP-p19-CBD protein are about 10× the molecular weight of the 17-25 base-paired dsRNA. This difference in size between the bound and unbound RNA can be detected by FP. Another method is quantum dot analysis such as described by Yezhelyev et al. *J Am Chem. Soc.* 130(28):9006-12 (2008)), which may also be used for detection of dsRNAs.

Examples of enzyme labels include methods in which for example a luciferase, green fluorescent protein or alkyl guanine DNA alkyl transferase are used. Small molecules such as biotin may be used. Biotin is linked to the polynucleotide probe, and avidin-bound enzymes, like horseradish peroxidase or alkaline phosphatase react with biotin through streptavidin to signal the presence of a molecule of interest. This is a standard method for ELISA detection of antibodies.

Immobilization of Reagents

The target RNA may be immobilized either directly or indirectly on or in a matrix. Indirect immobilization of the target RNA may occur by means of (a) hybridizing a target ssRNA to a matrix bound polynucleotide probe to form a small dsRNA which is subsequently recognized by a p19 fusion protein in solution; or (b) binding small dsRNA to p19 fusion protein bound to a matrix; or (c) binding dsRNA with p19 fusion protein in solution and then binding the complex to a matrix.

The p19 fusion protein can be readily immobilized on a matrix if that solid substrate is coated with a molecule with which the fusion protein binds, for example, chitin for binding chitin-binding domain or amylose for binding MBP. A polynucleotide probe can be bound to a matrix by means of a ligand such as biotin.

Examples of matrices include beads, columns, microtiter plates, a chip, or other 2-dimensional or three-dimensional formats known in the art. In addition, channels coated with chitin in microfluidic devices may be used to immobilize RNAs of interest.

Sensitivity of the Assay

Levels of enrichment of dsRNA of any sequence having a size preferably of greater than 17 nucleotides and less than 25 nucleotides can be achieved of greater than 20,000 fold and as much as 100,000 fold from total RNA. Moreover, as little as 10 μg of miRNA can be detected in a million-fold excess of total RNA and 50 μg of miRNA can be measured in total cell RNA from a tissue. Competitive gel shift data demonstrate that neither unbound single-stranded probe nor cytoplasmic RNA blocks binding of a miRNA and RNA probe in a p19 fusion protein detection assay.

Uses of the Assay

A specific polynucleotide probe may be attached to a substrate such as a plate or beads using standard methodology (for example biotin-steptavidin labeling) and exposed to a cell lysate from, for example, a biopsy. Only ssRNA of a specific sequence contained in the cell lysate will bind the immobilized polynucleotide probe. Labeled p19 fusion protein may then bind to the dsRNA or RNA/DNA hybrid and can be detected. FIGS. 17 and 18 demonstrate the feasibility of this approach for the quantitative detection of mir122a miRNA in total RNA extract from rat liver. Examples 4 and 5, FIGS. 17 and 18 illustrate how radioactive labeling or fluorescent-labeling is effective in detecting small amounts of the target miRNA in total lysate.

The labeled p19 fusion protein may either be in solution and optionally subsequently immobilized or already immobilized on a coated matrix (for example, chitin) where for example, the matrix is magnetic beads or the well of a microtiter plate. Accordingly, unbound material can be removed and the target RNA can be subsequently eluted from the matrix for analysis.

This approach can be adapted for high throughput screening of samples for target miRNAs (FIG. 14). Automation of detection can be facilitated using magnetic beads. For example, a biotinylated probe, previously hybridized to a miRNA target, can be linked to a plate coated with streptavidin. In this way, a labeled p19 fusion protein provides a signal for detecting miRNA (FIG. 16).

In an embodiment, automation of detection for high throughput processing of samples is facilitated by scanning an ELISA plate for binding of modified p19 fusion protein with labeled double-stranded miRNA. The ELISA plate can be coated with chitin to which p19-CBD fusion proteins bind. The unbound RNA can be removed by washing the plate and the remaining bound RNA can be detected by means of the attached probe. If the probe contains biotin, then it can be linked to a chromogenic readout using avidin conjugated to alkaline phosphatase or horseradish peroxidase (FIG. 15). An ELISA plate format for miRNA detection has many advantages. There exists an extensive amount of instrumentation for washing, reading and handling of ELISA plates. High throughput analysis is an important feature of analyzing clinical samples.

The methods and compositions described herein may be used to quantitatively determine the presence and amounts of endogenous miRNAs for purposes that include diagnosis or analyzing a wide range of pathologies such as cancers including determining the tissue of origin of the metastasized cancer, neuropathologies, and pathologies in other organs. These methods provide rapid, cost effective, efficient and scaleable detection of miRNAs in vitro.

All references cited herein, as well as U.S. provisional application Ser. No. 60/983,503 filed Oct. 29, 2007 and international application number PCT/US08/081,520 filed on Oct. 29, 2008 are incorporated by reference.

EXAMPLES

Example 1

Cloning of the D19 Fusion Protein and Binding to Size-Specific dsRNA

The p19 protein from the Carnation Italian ringspot virus codes for a 19 kDa protein and has a binding preference for 17-25 bp RNAs (Vargason et al. *Cell* 115:799-811) (2003)).

Sequence of the p19 protein from the Carnation Italian ringspot virus is as follows:

```
                                                       (SEQ ID NO: 1)
  1 MERAIQGNDT REQANGERWD GGSGGITSPF KLPDESPSWT EWRLYNDETN SNQDNPLGFK

61 ESWGFGKVVF KRYLRYDRTE ASLHRVLGSW TGDSVNYAAS RFLGANQVGC TYSIRFRGVS

121 VTISGGSRTL QHLCEMAIRS KQELLQLTPV EVESNVSRGC PEGIETFKKE SE
```

The plasmid vector pMAL-c2G from New England Biolabs (NEB, Ipswich, Mass.), was cleaved with PstI and HindIII, within the multiple cloning site. The following two PCR primers were used to amplify the chitin-binding domain, CBD, from the plasmid pTYB1 from New England Biolabs (NEB, Ipswich, Mass.): 5' G ACT CTG CAG ACG ACA AAT CCT GGT GTA TCC GCT 3' (SEQ ID NO:34) CBD (PstI) forward primer and 5' T AGG AAG CTT TCA TTG AAG CTG CCA CAA GGC AGG AAC 3' (SEQ ID NO:35) CBD (HindIII) reverse primer. After amplification the PCR product was cleaved with Pst I and Hind III and cloned into the plasmid pMAL-c2G. The new vector was then cleaved with BamHI. The p19 fusion protein coding sequencing, accession number NC 003500, was amplified with two primers containing BamHI sites. The PCR products was cleaved with BamHI and then cloned into the MBP CBD vector described above. The resulting plasmid construct coded for a fusion protein that contained an amino terminal MBP and a carboxy terminal CBD.

The MBP-p19-CBD fusion protein was isolated in high yields by binding and elution from amylose resin. The fusion protein was shown to be functionally active as described below.

Figure 3:
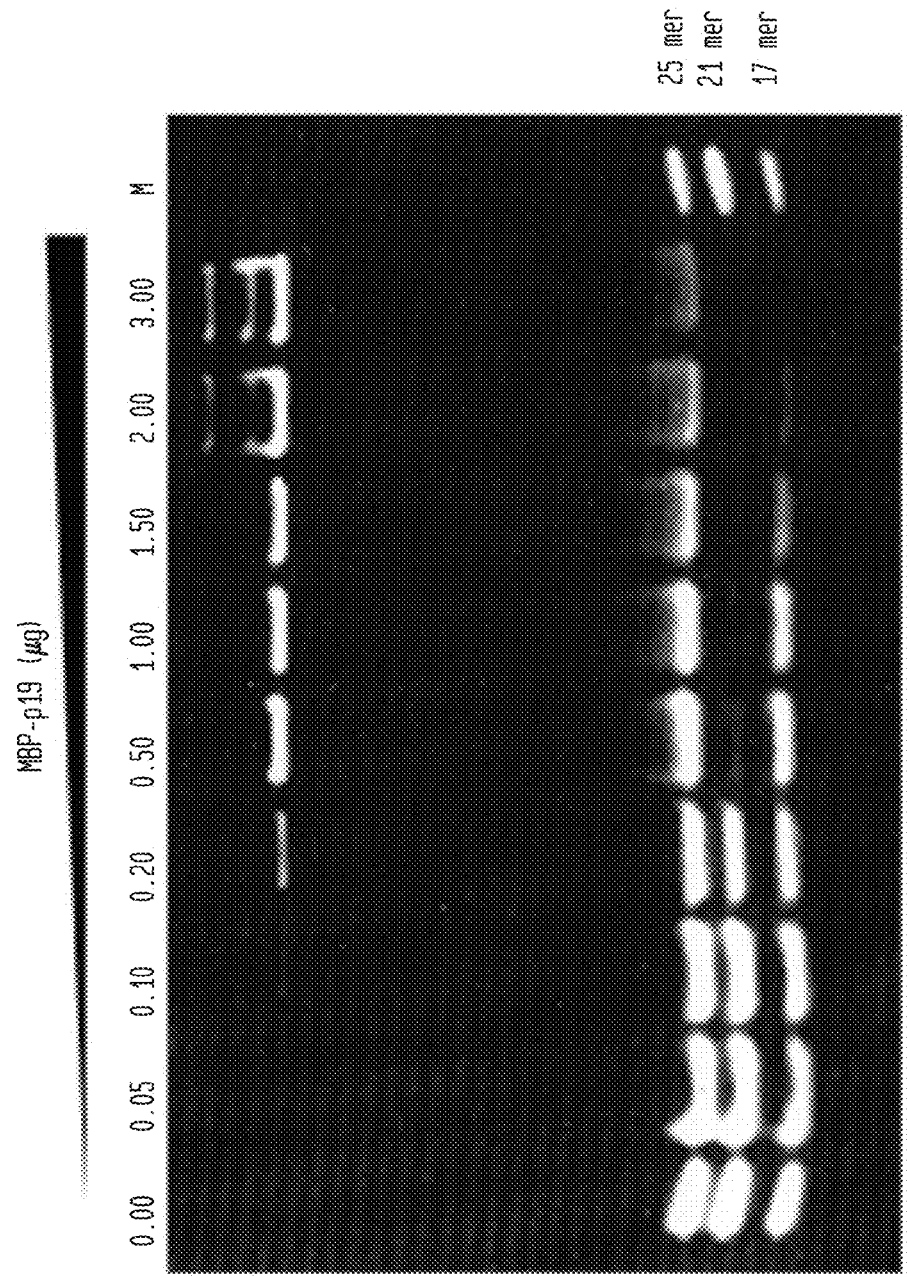
FIG. 3 demonstrates that the p19 fusion protein (MBP-p19-CBD) preferentially binds dsRNA of 21 nucleotides (nt) but does not bind dsRNA of 25 nucleotides or 17 nucleotides long. 0.5 μg of MBP-p19 fusion protein bound to 30 ng of the 21-mer dsRNA in a 20 μl reaction. The reaction also contained 30 ng of the 17-mer and 25-mer dsRNA. Lanes 1-9 show use of increasing amounts of MBP-p19-CBD fusion protein (μg) and lane 10 is a size marker.

The MBP-p19-CBD fusion protein (FIG. 19) was shown to bind an siRNA in a size-dependent sequence-independent manner where the size was preferably greater than 17 nucleotides and smaller than 25 nucleotides (FIG. 3). It was concluded that the presence of a large, 42 kDa, fusion partner like MBP does not have a major effect on siRNA binding to p19 fusion protein (FIG. 2).

The affinity of the p19 fusion protein for different substrates was determined by gel shift analysis (FIGS. 5 and 7). The affinity of p19 fusion protein was greater for siRNAs than for miRNAs which contained mismatched base pairs. The p19 fusion protein bound to 21-mer dsRNA/DNA hybrid but not to dsDNA of the same size or ssRNA, single-stranded DNA or ribosomal RNA. Binding of RNA to p19 was also detected by fluorescence-polarization studies that used fluorescent-labeled RNA (FIGS. 5, 7 and 9).

The MBP-p19-CBD fusion protein was used for siRNA isolation (FIGS. 12 and 13). Small RNAs that bound to the p19 fusion protein were purified with chitin magnetic beads. The CBD portion of the p19 fusion protein attached the dsRNA:protein complex to the beads (FIGS. 14 to 16). Background binding could be reduced with the addition of bovine serum albumin (BSA). The small RNAs were eluted from the chitin beads by denaturing the protein with 0.5% SDS.

Figure 4A:
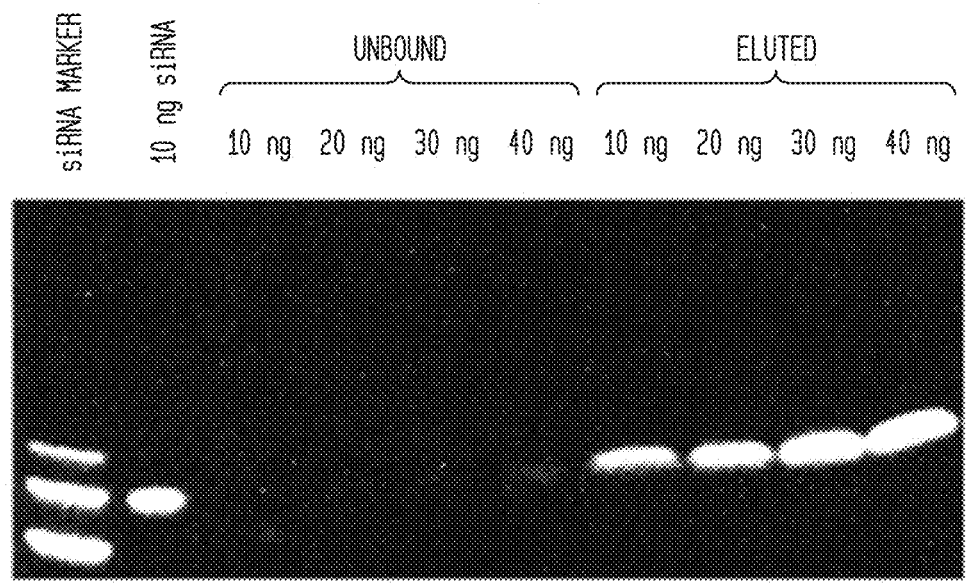
FIGS. 4A-4B show additional characterization of the p19 fusion protein.
Figure 4B:
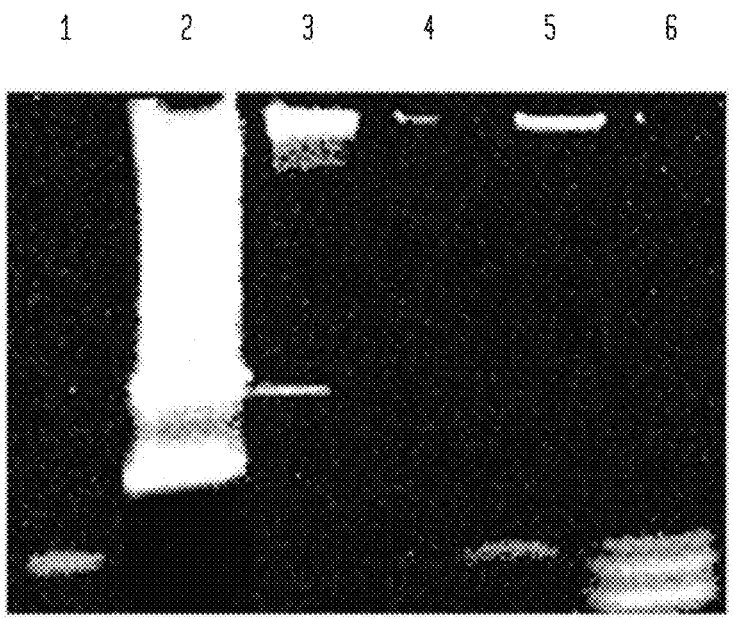

In a reconstruction experiment, a defined amount of siRNA was added to total rat liver RNA, bound to p19 fusion protein, concentrated with chitin magnetic beads and eluted. Greater then 5,000× enrichment was obtained using this approach (FIGS. 3 and 4).

Example 2

Determination of the Sensitivity and Quantification of the Detection Method for RNAs Using p19 Fusion Protein and Liquid Scintillation A method was developed using $^{32}$P-labeled polynucleotide probes to detect and quantify the abundance of endogenous miRNA in a total RNA sample. The p19 fusion protein specifically detected a hybrid between a miRNA and a labeled radioactive RNA probe in a one million-fold excess of cytoplasmic RNA. This was demonstrated using the abundant liverspecific miRNA, miR122a. A standard curve was made using increasing amounts of synthetic miR122a mixed with a large excess of JURKAT total RNA (T lymphocyte cell) to mimic assay conditions. JURKAT cell total RNA did not contain any detectable miR122a by this method. Variable amounts of miR122a oligo were hybridized to a constant amount or radioactive RNA probe, which was complementary to miR122a. A background standard lacking any added miR122a oligo was processed in the same as the samples (FIG. 17).

A quantitative measurement of endogenous miR122a was made by incubating rat liver total RNA with the miR122a specific probe. Three assays with different amounts of rat liver total RNA were performed to ensure concordance of the results. After hybridization, each sample was incubated with p19 fusion protein-coated magnetic beads to allow for binding of the miR122a-probe duplex. To remove the unbound RNA, p19 fusion protein beads were washed 5 times and the miR122a duplex was eluted from the beads by denaturing p19 fusion protein with an elution buffer containing 0.5% SDS. The eluted radioactive duplex was counted and the background control was subtracted from each sample. To demonstrate that the radioactivity corresponded to the miR122a/probe, the eluent was loaded on an acrylamide gel (FIG. 5A) and exposed to X-ray film. As observed on the autoradiograph, the eluted RNA was double-stranded, not single-stranded probe.

After subtracting the control radioactive count from each result, the standard counts corresponding to the miR122a duplex were plotted as a function of synthetic miR122a amount (FIG. 5B). A linear curve demonstrated the proportionality between the radioactive signal and the amount of miR122a complex. Comparison to the standard curve provides a relative measurement of the miR122a abundance in a physiological sample (FIGS. 5C and 5D). A value of 50 pg+/−12 μg of miR122a per μg of rat liver total RNA was obtained for the three concentrations of RNA. The detection is linear over two orders of magnitude and has a sensitivity of 2-5 pg of miRNA.

(a) Labeling miR122a Probe Using $\gamma$-$^{32}$P-ATP

In a microfuge tube, 300 ng of miR122a probe (5' OH-aacaccauugucacacuccaua) was added to 2 μL of T4 polynucleotide kinase reaction buffer (70 mM Tris-HCl (pH7.6), 10 mM MgCl2, 5 mM dithiothreitol from New England Biolabs (NEB, Ipswich, Mass.)) and 3 μL of miliQ water. Then, 10 μL of $\gamma$-$^{32}$P-ATP (PerkinElmer, Waltham, Mass.) at 6,000 Ci/mmol and 2 μL of T4 polynucleotide kinase (10,000 units/mL) from New England Biolabs (NEB, Ipswich, Mass.) were added to the labeling reaction. The reaction tube was placed in a 37° C. heat block for 40 to 60 minutes, and then the reaction was stopped by inactivating the enzyme at 65° C. for 20 minutes. After stopping the reaction, the entire labeling reaction was loaded onto a CentriSep column (Princeton Separation, Freehold, N.J.) and centrifuged for 2 minutes at 3,000 rpm to remove the excess $\gamma$-$^{32}$P-ATP. The specific activity of labeled probe was determined by counting 1 μL of a ten-fold dilution of the purified labeling reaction in a scintillation counter.

(b) Total RNA Extraction from JURKAT Cells

JURKAT total RNA was obtained using Trizol (Invitrogen, Carlsbad, Calif.) as recommended by the manufacturer. 10 mL of Trizol were added to the JURKAT cell pellet. The sample was transferred in a 30 mL tube and cells were disrupted by homogenization using a syringe. After complete homogenization, the tube was incubated 5 minutes at room temperature to permit the complete dissociation of nucleoprotein complex. 2 mL of chloroform was added to the sample, vortexed for 15 seconds and incubated at room temperature for 2 to 3 minutes and centrifuged at 4° C. for 15 minutes at 12,000 g. To precipitate the RNA sample, the aqueous phase was transferred to a new tube containing 5 mL of isopropanol, placed at room temperature for 10 minutes and centrifuged at 4° C. for 10 minutes at 12,000 g. The RNA pellet was then washed with 10 mL 75% ethanol and thoroughly drying. The pellet was resuspended with 200 μL of sterile Tris-EDTA. The total RNA concentration was estimated via optical density using the nanodrop spectrophotometer and the purity was evaluated by the ratio A260 nm/A280 nm.

(c) Assay for Small RNAs

RNA samples were added to loading buffer and loaded into pre-rinsed wells of a TBE Gel 20% acrylamide (Invitrogen, Carlsbad, Calif.) as well as the RNA size marker (siRNA Marker, New England Biolabs (NEB, Ipswich, Mass.)). After running at 100V for 2 hours, the gel was stained with SybrGold (Invitrogen, Carlsbad, Calif.) and visualized on a fluorimager. In the competitive binding assays of RNA/DNA to p19 fusion protein, the gels were exposed to X-ray film and the bands scanned to determine relative binding affinities.

(d) Quantification of Endogenous miR122a Using p19 Fusion Protein-Based Liquid Scintillation miRNA Detection Method Quantification of sensitivity was determined by (1) varying amounts of total rat liver RNA (2, 5 and 10 μg) incubated with 1 ng of specific probe; and (2) varying amounts of miRI22a RNA (target RNA) (500 pg to 0.32 pg).

A miR122a complementary sequence was synthesized and labeled with a radioactive label. Specifically, 5' $\gamma$-$^{32}$P aacaccauugucacacuccaua (SEQ ID NO:2) was labeled at the 5' end using $\gamma$-$^{32}$P-ATP. Incubation was performed 2 hours at 65° C. in 1×p19 fusion protein binding buffer (20 mM Tris HCl, 100 mM NaCl, 1 mM EDTA and 1 mM TCEP, pH 7 at 25° C.). The labeled probe was mixed with miR122a RNA and total JURKAT RNA and incubated for 2 hours at 65° C. to allow hybridization between the target miR122a and the probe.

Hybridized dsRNA was allowed to bind to p19 fusion protein coated beads. These beads were made as follows: Chitin magnetic beads (NEB#E8036) were pretreated with BSA by washing the beads in 1×BSA buffer (20 mM Tris HCl, 100 mM NaCl, 1 mM EDTA, 1 mM TCEP and BSA at 1 mg/mL pH 7 at 25° C.) twice using a magnetic rack (New England Biolabs #S1506S (NEB, Ipswich, Mass.)) and resuspended in the same buffer and incubated overnight at 4° C. p19 fusion protein-bound magnetic beads were made by mixing p19-CBD fusion protein with pretreated chitin beads (30 μg p19 fusion protein for 200 μl beads suspension) in 200 μL 1×p19 fusion protein binding buffer with 1 mg/mL BSA and incubated at 4° C. overnight. The subsequent protein beads were stored at 4° C.

Binding of miR122a-probe duplex to p19 fusion protein occurred when 10 μL of the p19 fusion protein-coated magnetic beads were incubated for 1.5 hours at room temperature in an orbital shaker in 1×p19-binding buffer containing RNAse inhibitor and BSA at 1 mg/mL. Unbound RNA was eliminated by washing the beads 5 times with 500 μL 1×p19 fusion protein wash buffer prewarmed at 37° C. (20 mM Tris HCl, 100 mM NaCl, 1 mM EDTA and 1 mM TCEP, pH 7 at 25° C.) shaking for 5 minutes at room temperature.

miR122a-probe duplex was eluted from the beads with 20 μL of 1×p19 fusion protein elution buffer (20 mM Tris HCl, 100 mM NaCl, 1 mM EDTA and 0.5% SDS, pH 7 at 25° C.) after incubation 10 minutes at 37° C. followed by mixing 10 minutes at room temperature. The beads were spun down and the supernatant was removed. 18 μL of the elution were loaded on 20% acrylamide gel (Invitrogen, Carlsbad, Calif.)

using TBE buffer and 2 μL of the eluted RNA were used for radioactive counting. The results are shown in FIG. 17.

(E) Qualitative Detection of Let-7a Using p19 Fusion Protein-Based Liquid Scintillation miRNA Detection Method miRNA Let-7a was detected in JURKAT total RNA as follows: Three samples were prepared containing different amounts of JURKAT total RNA. JURKAT total RNA was incubated with the Let-7a specific probe to allow hybridization between the target and probe. The probe was a synthetic Let-7a complementary sequence labeled at the 5' end using γ-$^{32}$P-ATP. After hybridization, the three samples containing the potential Let-7a complex were incubated with p19 fusion protein-coated beads.

To remove the unbound RNA and the excess single-stranded probe, p19 fusion protein coated beads were washed 5 times and the Let-7a complex was eluted from the beads by denaturing p19 fusion protein with an elution buffer containing 0.5% SDS. The radioactivity in each sample was measured using liquid scintillation counting. To ensure that the radioactive count corresponded to the signal of the Let-7a duplex, the rest of the elution was separated and autoradiographed (FIG. 7).

The results confirmed that Let-7a miRNA was present in the JURKAT cell line at detectable levels by gel electrophoresis and scintillation counting.

Different samples containing various amount of JURKAT total RNA were incubated with 600 μg of a specific RNA probe (synthetic Let-7a complementary sequence, 5' γ-$^{32}$P-cuauacaaccuacuaccucaaa) (SEQ ID NO:2) labeled at the 5' end using γ-$^{32}$P-ATP. Incubation was performed for 2 hours at 65° C. in 1×p19 fusion protein binding buffer (20 mM Tris HCl, 100 mM NaCl, 1 mM EDTA and 1 mM TCEP, pH 7 at 25° C.) to allow hybridization between the target Let-7a and the RNA probe. In order for the p19 fusion protein-coated beads to recognize the Let-7a-probe duplex, the solution containing miRNA duplex was incubated with p19 fusion protein beads (from 10 μL of a suspension of p19 fusion protein coated beads) for 1.5 hours at room temperature in 1×p19 fusion protein binding buffer containing RNAse inhibitor and BSA at 1 mg/mL. Unbound RNA was eliminated by washing the beads 5 times with 500 μL 1×p19 fusion protein wash buffer pre-warmed at 37° C. (20 mM Tris HCl, 100 mM NaCl, 1 mM EDTA and 1 mM TCEP, pH 7 at 25° C.) shaking for 5 minutes at room temperature. The Let-7a-probe duplex was eluted from the beads with 20 μL of 1×p19 fusion protein elution buffer (20 mM Tris HCl, 100 mM NaCl, 1 mM EDTA and 0.5% SDS, pH 7 at 25° C.) after incubation 10 minutes at 37° C. followed by mixing 10 minutes at room temperature. The beads were spun down and the supernatant was removed. 18 μL of the elution were loaded on TBE 20% acrylamide gel (Invitrogen, Carlsbad, Calif.) and 2 μL were used for radioactive counting. The results are shown in FIG. 18.

(f) Binding of p19 Fusion Protein to miRNA/RNA polyA-Tail Probe

To improve the sensitivity of detection, p19 fusion protein binding to a miRNA hybridized to a longer RNA probe was tested. Synthetic miR122a was hybridized to a FAM-labeled probe containing a 20 to 30 base poly A-tail. The hybrid obtained was incubated with p19 fusion protein and separated by PAGE electrophoresis and stained by SybrGold (Invitrogen, Carlsbad, Calif.). A mobility shift was observed when the hybrid was incubated with the p19 fusion protein. No shift was observed in the sample without p19 fusion protein. This result demonstrated that p19 fusion protein binds a miRNA/RNA polyA-tail probe (FIG. 8) and may be used in future detection methods. An increase in the length of the polynucleotide probe allows for increased sensitivity of detection.

10 ng of synthetic miR122a was hybridized to 10 ng of probe containing a non-radioactive 3' polyA-tail (5' P-aacac-cauugucacacuccaua-polyA tail) (SEQ ID NO:2) at 65° C. for 10 minutes. The hybrid obtained was incubated with 1.5 μg of p19 fusion protein (New England Biolabs (NEB, Ipswich, Mass.)) at room temperature for 1.5 hours in binding buffer (20 mM Tris HCl, 100 mM NaCl, 1 mM EDTA, 1 mM TCEP, pH 7 at 25° C.), to allow binding. A sample without p19 fusion protein was performed in identical condition as a control. The two samples were loaded on 20% acrylamide gel in TBE buffer (Invitrogen, Carlsbad, Calif.) and stained by SybrGold (Invitrogen, Carlsbad, Calif.).

Example 3

A p19 Fusion Protein-Based RNA Detection Method Using a Fluorescent-Labeled Polynucleotide Probe A standard curve using a synthetic FAM-labeled RNA probe (FIG. 9) complementary to miR31 was created. A background standard without synthetic miR31 was processed in a similar way. The hybridization step was performed in presence of a large excess of JURKAT total RNA. JURKAT cells do not have miR31. Each sample was processed in triplicate to ensure concordance of the results. After hybridization, each sample was incubated with p19 fusion protein-coated magnetic beads to allow recognition between miR31-probe duplex and p19 fusion protein protein. To remove unbound RNA, p19 fusion protein beads were washed twice and the miR31 duplex was eluted from the beads by denaturing p19 fusion protein with an elution buffer containing 0.5% SDS. Fluorescence of the samples was read with an excitation wavelength of 485 nm, an emission wavelength of 520 nm and a cutoff of 495 nm. The background signal was subtracted from each standard to remove the signal due to non-specific binding to the beads. For each triplicate, we calculated the average and standard deviation. The average of standard Relative Fluorescence Unit (RFU) corresponding to the miR31 duplex was plotted as a function of synthetic miR31. A linear graph demonstrated the proportionality between the fluorescent signal and the amount of the miR31 complex.

To increase the sensitivity and reduce the variability, each component of the buffer was analyzed to determine which reagents might cause a shift or a quenching of the specific fluorescence signal. To reduce the fluorescent background, each buffer and sample were maintained in the absence of UV absorbing compounds and dust. Excitation scans obtained demonstrated that the [tris (2-carboxyethyl)phosphine] (TCEP) contained in each buffer quenched the fluorescent signal (FIG. 11A). Unmodified binding buffer absent TCEP and BSA (20 mM Tris-HCl, 100 mM NaCl, 1 mM EDTA, pH 7.0 at 25° C.) was used. Sensitivity tests were performed to define the best conditions for optimal sensitivity. The sensitivity was higher when the miRNA was in an elution buffer containing 0.1M NaOH (detect 5 μg) compared with an elution buffer containing SDS 0.5% (detect 40 μg) (FIG. 12). Elution of the miRNA complex from the p19 fusion protein beads was performed using an alkaline buffer containing 0.1 M NaOH.

Fluorescence of the samples was read with an excitation wavelength of 492 nm, an emission wavelength of 520 nm and a cutoff of 515 nm. The background signal was subtracted from each sample. Reactions were in triplicate. The average of standard Relative fluorescence units (RFU) corresponding to the miR31 duplex was plotted as a function of synthetic miR31 amount. The detection is linear. The variability of the detection protocol was markedly reduced in alkaline buffer with a detection limit of 10 μg compare to 5 ng for the previous experiment suggesting reduced fluorescence background and a higher sensitivity of detection.

We claim:

1. A method; comprising:
   (a) hybridizing a single-stranded target RNA having a first length, to a complementary polynucleotide probe having a second length, to form a double-stranded hybrid polynucleotide;
   (b) reacting the double-stranded hybrid with a p19 fusion protein wherein the p19 fusion protein or the target RNA is labeled, wherein the label is
      (i) directly linked to the protein or target RNA, or
      (ii) indirectly linked by a molecule capable of binding to the p19 fusion protein or target RNA; and
   (c) detecting target RNA bound to the p19 fusion protein wherein the target RNA bound to the p19 fusion protein is optionally immobilized on a matrix.

2. A method according to claim 1, wherein the first length and the second length are different.

3. A method according to claim 1, wherein the complementary polynucleotide probe is an RNA, a DNA molecule or a locked nucleic acid.

4. A method according to claim 1, wherein the complementary polynucleotide probe extends at the 3' end beyond the target RNA.

5. A method according to claim 1, wherein the single-stranded molecule is an miRNA.

6. A method according to claim 1, wherein the first and the second length are the same.

7. A method according to claim 1, herein the p19 fusion protein is immobilized prior to binding the target RNA.

8. A method according to claim 1, wherein the target RNA is immobilized prior to binding the p19 fusion protein.

9. A method according to claim 1, wherein the detectable label is selected from the group consisting of a fluorescent label, a radioactive label, a chemiluminescent label, a protein label and a small molecule label.

10. A method according to claim 1, wherein the p19 fusion protein is bound to the target RNA to form a complex which is then immobilized on a matrix.

11. A method according to claim 1, wherein the matrix has a colored or fluorescent label that differs from the label on the p19 protein or polynucleotide probe.

12. A method according to claim 1, wherein the matrix is a bead.

13. A method according to claim 12, wherein the bead is magnetic.

14. A method according to claim 12, wherein the bead is coated with a carbohydrate to which the p19 fusion protein can bind.

15. A method according to claim 1, wherein the immobilized target RNA is diagnostic for an abnormal condition of a cell.

16. A method according to claim 1, wherein the target RNA is diagnostic of an abnormal host cell and is present in a mixture comprising a plurality of types and sizes of RNA.

17. The method according to claim 1, wherein the p19 fusion protein has a carbohydrate-binding protein at one end of the protein.

18. The method of claim 17 wherein the carbohydrate-binding protein is a maltose-binding protein (MBP), chitin-binding domain (CBD) or a cellulose-binding domain.

19. A method; comprising:
   mixing a target RNA with a recombinant RNA-binding protein having at least 90% sequence homology to SEQ ID NO: 33, wherein either the recombinant RNA-binding protein or the target RNA is labeled, the label being
      (i) directly linked to the recombinant RNA-binding protein or target RNA, or
      (ii) indirectly linked by a molecule that binds to the recombinant RNA-binding protein or target RNA; and
   detecting target RNA bound to the recombinant RNA-binding protein wherein the target RNA bound to the recombinant RNA-binding protein is immobilized on a matrix.

* * * * *

SEQUENCE LISTING

<160> NUMBER OF SEQ ID NOS: 35

<210> SEQ ID NO 1
<211> LENGTH: 172
<212> TYPE: PRT
<213> ORGANISM: Carnation Italian ringspot virus

<400> SEQUENCE: 1

```
Met Glu Arg Ala Ile Gln Gly Asn Asp Thr Arg Glu Gln Ala Asn Gly
1               5                   10                  15

Glu Arg Trp Asp Gly Gly Ser Gly Gly Ile Thr Ser Pro Phe Lys Leu
            20                  25                  30

Pro Asp Glu Ser Pro Ser Trp Thr Glu Trp Arg Leu Tyr Asn Asp Glu
        35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Leu Gly Ala Asn Gln Val Gly Cys Thr Tyr
            100                 105                 110

Ser Ile Arg Phe Arg Gly Val Ser Val Thr Ile Ser Gly Gly Ser Arg
        115                 120                 125

Thr Leu Gln His Leu Cys Glu Met Ala Ile Arg Ser Lys Gln Glu Leu
    130                 135                 140

Leu Gln Leu Thr Pro Val Glu Val Glu Ser Asn Val Ser Arg Gly Cys
145                 150                 155                 160

Pro Glu Gly Ile Glu Thr Phe Lys Lys Glu Ser Glu
                165                 170
```

<210> SEQ ID NO 2
<211> LENGTH: 22
<212> TYPE: RNA
<213> ORGANISM: unknown
<220> FEATURE:
<223> OTHER INFORMATION: completely synthetic

<400> SEQUENCE: 2
aacaccauug ucacacucca ua 22

<210> SEQ ID NO 3
<211> LENGTH: 80
<212> TYPE: RNA
<213> ORGANISM: Homo sapiens

<400> SEQUENCE: 3
ugggaugagg uaguagguug uauaguuuua gggucacacc caccacuggg agauaacuau 60
acaaucuacu gucuuuccua 80

<210> SEQ ID NO 4
<211> LENGTH: 21
<212> TYPE: RNA
<213> ORGANISM: unknown
<220> FEATURE:
<223> OTHER INFORMATION: synthetic oligonucleotide

<400> SEQUENCE: 4
cguacgcgga auacuucgau u 21

<210> SEQ ID NO 5
<211> LENGTH: 21
<212> TYPE: RNA
<213> ORGANISM: unknown
<220> FEATURE:
<223> OTHER INFORMATION: synthetic oligonucleotide

<400> SEQUENCE: 5
ucgaaguauu ccgcguacgu u                                              21

<210> SEQ ID NO 6
<211> LENGTH: 17
<212> TYPE: RNA
<213> ORGANISM: unknown
<220> FEATURE:
<223> OTHER INFORMATION: synthetic oligonucleotide

<400> SEQUENCE: 6
cucaaccagc cacugcu                                                   17

<210> SEQ ID NO 7
<211> LENGTH: 17
<212> TYPE: RNA
<213> ORGANISM: unknown
<220> FEATURE:
<223> OTHER INFORMATION: synthetic oligonucleotide

<400> SEQUENCE: 7
caguggcugg uugagau                                                   17

<210> SEQ ID NO 8
<211> LENGTH: 25
<212> TYPE: RNA
<213> ORGANISM: unknown
<220> FEATURE:
<223> OTHER INFORMATION: synthetic oligonucleotide

<400> SEQUENCE: 8
cguacgcgga auacuucgaa auguu                                          25

<210> SEQ ID NO 9
<211> LENGTH: 25
<212> TYPE: RNA
<213> ORGANISM: unknown
<220> FEATURE:
<223> OTHER INFORMATION: synthetic oligonucleotide

<400> SEQUENCE: 9
cauuucgaag uauuccgcgu acguu                                          25

<210> SEQ ID NO 10
<211> LENGTH: 21
<212> TYPE: RNA
<213> ORGANISM: unknown
<220> FEATURE:
<223> OTHER INFORMATION: synthetic oligonucleotide

<400> SEQUENCE: 10
cguacgcgga auacuucgau u                                              21

<210> SEQ ID NO 11
<211> LENGTH: 21
<212> TYPE: RNA
<213> ORGANISM: unknown
<220> FEATURE:
<223> OTHER INFORMATION: synthetic oligonucleotide

```
<400> SEQUENCE: 11
ucgaaguauu ccgcguacgu u                                              21

<210> SEQ ID NO 12
<211> LENGTH: 21
<212> TYPE: RNA
<213> ORGANISM: unknown
<220> FEATURE:
<223> OTHER INFORMATION: synthetic oligonucleotide

<400> SEQUENCE: 12
cguacgcgga auacuucgau u                                              21

<210> SEQ ID NO 13
<211> LENGTH: 19
<212> TYPE: RNA
<213> ORGANISM: unknown
<220> FEATURE:
<223> OTHER INFORMATION: synthetic oligonucleotide

<400> SEQUENCE: 13
cguacgcgga auacuucga                                                 19

<210> SEQ ID NO 14
<211> LENGTH: 19
<212> TYPE: RNA
<213> ORGANISM: unknown
<220> FEATURE:
<223> OTHER INFORMATION: synthetic oligonucleotide

<400> SEQUENCE: 14
cguacgcgga auacuucga                                                 19

<210> SEQ ID NO 15
<211> LENGTH: 21
<212> TYPE: RNA
<213> ORGANISM: unknown
<220> FEATURE:
<223> OTHER INFORMATION: synthetic oligonucleotide

<400> SEQUENCE: 15
acguacgcgg aauacuucga u                                              21

<210> SEQ ID NO 16
<211> LENGTH: 21
<212> TYPE: RNA
<213> ORGANISM: unknown
<220> FEATURE:
<223> OTHER INFORMATION: synthetic oligonucleotide

<400> SEQUENCE: 16
cguacgcgga auacuucgau u                                              21

<210> SEQ ID NO 17
<211> LENGTH: 21
<212> TYPE: DNA
<213> ORGANISM: unknown
<220> FEATURE:
<223> OTHER INFORMATION: synthetic oligonucleotide

<400> SEQUENCE: 17
tcgaagtatt ccgcgtacgt t                                              21

<210> SEQ ID NO 18
<211> LENGTH: 21
```

```
<212> TYPE: DNA
<213> ORGANISM: unknown
<220> FEATURE:
<223> OTHER INFORMATION: synthetic oligonucleotide

<400> SEQUENCE: 18
cgtacgcgga atacttcgat t                                             21

<210> SEQ ID NO 19
<211> LENGTH: 21
<212> TYPE: DNA
<213> ORGANISM: unknown
<220> FEATURE:
<223> OTHER INFORMATION: synthetic oligonucleotide

<400> SEQUENCE: 19
tcgaagtatt ccgcgtacgt t                                             21

<210> SEQ ID NO 20
<211> LENGTH: 21
<212> TYPE: RNA
<213> ORGANISM: unknown
<220> FEATURE:
<223> OTHER INFORMATION: synthetic oligonucleotide

<400> SEQUENCE: 20
cguacgcgga auacuucgau u                                             21

<210> SEQ ID NO 21
<211> LENGTH: 21
<212> TYPE: DNA
<213> ORGANISM: unknown
<220> FEATURE:
<223> OTHER INFORMATION: synthetic oligonucleotide
<220> FEATURE:
<221> NAME/KEY: misc_feature
<222> LOCATION: (7)..(7)
<223> OTHER INFORMATION: This position contains FAM covalently linked to
      thymadine; FAM is 5-[(N-(3'-diphenylphosphinyl-4'-
      methoxycarbonyl)phenylcarbonyl)aminoacetamido]fluorescein

<400> SEQUENCE: 21
ucgaagtauu ccgcguacgu u                                             21

<210> SEQ ID NO 22
<211> LENGTH: 21
<212> TYPE: RNA
<213> ORGANISM: unknown
<220> FEATURE:
<223> OTHER INFORMATION: synthetic oligonucleotide

<400> SEQUENCE: 22
cguacgcgga auacuucgau u                                             21

<210> SEQ ID NO 23
<211> LENGTH: 22
<212> TYPE: RNA
<213> ORGANISM: Caenorhabditis elegans

<400> SEQUENCE: 23
ugagguagua gguuguauag uu                                            22

<210> SEQ ID NO 24
<211> LENGTH: 22
<212> TYPE: RNA
<213> ORGANISM: Caenorhabditis elegans

<400> SEQUENCE: 24
```
cuaugcaauu uucuaccuua cc                                              22

<210> SEQ ID NO 25
<211> LENGTH: 21
<212> TYPE: RNA
<213> ORGANISM: Gallus gallus

<400> SEQUENCE: 25
agagguagug gguugcauag u                                               21

<210> SEQ ID NO 26
<211> LENGTH: 21
<212> TYPE: RNA
<213> ORGANISM: Gallus gallus

<400> SEQUENCE: 26
uauacaaccu gcugccuuuc u                                               21

<210> SEQ ID NO 27
<211> LENGTH: 21
<212> TYPE: RNA
<213> ORGANISM: Caenorhabditis elegans

<400> SEQUENCE: 27
ugacuagaga cacauucagc u                                               21

<210> SEQ ID NO 28
<211> LENGTH: 22
<212> TYPE: RNA
<213> ORGANISM: Caenorhabditis elegans

<400> SEQUENCE: 28
cuggaugugc ucguuaguca ua                                              22

<210> SEQ ID NO 29
<211> LENGTH: 22
<212> TYPE: RNA
<213> ORGANISM: unknown
<220> FEATURE:
<223> OTHER INFORMATION: synthetic

<400> SEQUENCE: 29
uggaguguga caauggguguu ug                                             22

<210> SEQ ID NO 30
<211> LENGTH: 22
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (6)..(6)
<223> OTHER INFORMATION: This position contains FAM covalently linked to
      thymadine; FAM is 5-[(N-(3'-diphenylphosphinyl-4'-
      methoxycarbonyl)phenylcarbonyl)aminoacetamido]fluorescein

<400> SEQUENCE: 30
aacactauug ucacacucca ua                                              22

<210> SEQ ID NO 31
<211> LENGTH: 21
<212> TYPE: RNA
<213> ORGANISM: unknown
<220> FEATURE:
<223> OTHER INFORMATION: synthetic

<400> SEQUENCE: 31
ucgaaguauu ccgcguacgu u					21

<210> SEQ ID NO 32
<211> LENGTH: 1881
<212> TYPE: DNA
<213> ORGANISM: Carnation Italian ringspot virus
<220> FEATURE:
<221> NAME/KEY: CDS
<222> LOCATION: (1)..(1878)
<220> FEATURE:
<221> NAME/KEY: 1184CDS
<222> LOCATION: (1)..(1698)

<400> SEQUENCE: 32

| | | | | | | | | | | | | | | | | |
|---|---|---|---|---|---|---|---|---|---|---|---|---|---|---|---|---|
| atg | aaa | act | gaa | gaa | ggt | aaa | ctg | gta | atc | tgg | att | aac | ggc | gat | aaa | 48 |
| Met | Lys | Thr | Glu | Glu | Gly | Lys | Leu | Val | Ile | Trp | Ile | Asn | Gly | Asp | Lys | |
| 1 | | | | 5 | | | | | 10 | | | | | 15 | | |
| ggc | tat | aac | ggt | ctc | gct | gaa | gtc | ggt | aag | aaa | ttc | gag | aaa | gat | acc | 96 |
| Gly | Tyr | Asn | Gly | Leu | Ala | Glu | Val | Gly | Lys | Lys | Phe | Glu | Lys | Asp | Thr | |
| | | | 20 | | | | | 25 | | | | | 30 | | | |
| gga | att | aaa | gtc | acc | gtt | gag | cat | ccg | gat | aaa | ctg | gaa | gag | aaa | ttc | 144 |
| Gly | Ile | Lys | Val | Thr | Val | Glu | His | Pro | Asp | Lys | Leu | Glu | Glu | Lys | Phe | |
| | 35 | | | | | 40 | | | | | 45 | | | | | |
| cca | cag | gtt | gcg | gca | act | ggc | gat | ggc | cct | gac | att | atc | ttc | tgg | gca | 192 |
| Pro | Gln | Val | Ala | Ala | Thr | Gly | Asp | Gly | Pro | Asp | Ile | Ile | Phe | Trp | Ala | |
| 50 | | | | | 55 | | | | | 60 | | | | | | |
| cac | gac | cgc | ttt | ggt | ggc | tac | gct | caa | tct | ggc | ctg | ttg | gct | gaa | atc | 240 |
| His | Asp | Arg | Phe | Gly | Gly | Tyr | Ala | Gln | Ser | Gly | Leu | Leu | Ala | Glu | Ile | |
| 65 | | | | | 70 | | | | | 75 | | | | | 80 | |
| acc | ccg | gac | aaa | gcg | ttc | cag | gac | aag | ctg | tat | ccg | ttt | acc | tgg | gat | 288 |
| Thr | Pro | Asp | Lys | Ala | Phe | Gln | Asp | Lys | Leu | Tyr | Pro | Phe | Thr | Trp | Asp | |
| | | | | 85 | | | | | 90 | | | | | 95 | | |
| gcc | gta | cgt | tac | aac | ggc | aag | ctg | att | gct | tac | ccg | atc | gct | gtt | gaa | 336 |
| Ala | Val | Arg | Tyr | Asn | Gly | Lys | Leu | Ile | Ala | Tyr | Pro | Ile | Ala | Val | Glu | |
| | | | 100 | | | | | 105 | | | | | 110 | | | |
| gcg | tta | tcg | ctg | att | tat | aac | aaa | gat | ctg | ctg | ccg | aac | ccg | cca | aaa | 384 |
| Ala | Leu | Ser | Leu | Ile | Tyr | Asn | Lys | Asp | Leu | Leu | Pro | Asn | Pro | Pro | Lys | |
| | 115 | | | | | 120 | | | | | 125 | | | | | |
| acc | tgg | gaa | gag | atc | ccg | gcg | ctg | gat | aaa | gaa | ctg | aaa | gcg | aaa | ggt | 432 |
| Thr | Trp | Glu | Glu | Ile | Pro | Ala | Leu | Asp | Lys | Glu | Leu | Lys | Ala | Lys | Gly | |
| 130 | | | | | 135 | | | | | 140 | | | | | | |
| aag | agc | gcg | ctg | atg | ttc | aac | ctg | caa | gaa | ccg | tac | ttc | acc | tgg | ccg | 480 |
| Lys | Ser | Ala | Leu | Met | Phe | Asn | Leu | Gln | Glu | Pro | Tyr | Phe | Thr | Trp | Pro | |
| 145 | | | | | 150 | | | | | 155 | | | | | 160 | |
| ctg | att | gct | gct | gac | ggg | ggt | tat | gcg | ttc | aag | tat | gaa | aac | ggc | aag | 528 |
| Leu | Ile | Ala | Ala | Asp | Gly | Gly | Tyr | Ala | Phe | Lys | Tyr | Glu | Asn | Gly | Lys | |
| | | | | 165 | | | | | 170 | | | | | 175 | | |
| tac | gac | att | aaa | gac | gtg | ggc | gtg | gat | aac | gct | ggc | gcg | aaa | gcg | ggt | 576 |
| Tyr | Asp | Ile | Lys | Asp | Val | Gly | Val | Asp | Asn | Ala | Gly | Ala | Lys | Ala | Gly | |
| | | | 180 | | | | | 185 | | | | | 190 | | | |
| ctg | acc | ttc | ctg | gtt | gac | ctg | att | aaa | aac | aaa | cac | atg | aat | gca | gac | 624 |
| Leu | Thr | Phe | Leu | Val | Asp | Leu | Ile | Lys | Asn | Lys | His | Met | Asn | Ala | Asp | |
| | 195 | | | | | 200 | | | | | 205 | | | | | |
| acc | gat | tac | tcc | atc | gca | gaa | gct | gcc | ttt | aat | aaa | ggc | gaa | aca | gcg | 672 |
| Thr | Asp | Tyr | Ser | Ile | Ala | Glu | Ala | Ala | Phe | Asn | Lys | Gly | Glu | Thr | Ala | |
| 210 | | | | | 215 | | | | | 220 | | | | | | |
| atg | acc | atc | aac | ggc | ccg | tgg | gca | tgg | tcc | aac | atc | gac | acc | agc | aaa | 720 |
| Met | Thr | Ile | Asn | Gly | Pro | Trp | Ala | Trp | Ser | Asn | Ile | Asp | Thr | Ser | Lys | |
| 225 | | | | | 230 | | | | | 235 | | | | | 240 | |
| gtg | aat | tat | ggt | gta | acg | gta | ctg | ccg | acc | ttc | aag | ggt | caa | cca | tcc | 768 |

-continued

| | | | | | | | | | | | | | | | |
|---|---|---|---|---|---|---|---|---|---|---|---|---|---|---|---|
| Val | Asn | Tyr | Gly | Val | Thr | Val | Leu | Pro | Thr | Phe | Lys | Gly | Gln | Pro | Ser |
| | | | | 245 | | | | 250 | | | | | 255 | | |

| aaa | ccg | ttc | gtt | ggc | gtg | ctg | agc | gca | ggt | att | aac | gcc | gcc | agt | ccg | 816 |
|---|---|---|---|---|---|---|---|---|---|---|---|---|---|---|---|---|
| Lys | Pro | Phe | Val | Gly | Val | Leu | Ser | Ala | Gly | Ile | Asn | Ala | Ala | Ser | Pro | |
| | | | 260 | | | | | 265 | | | | | 270 | | | |

| aac | aaa | gag | ctg | gca | aaa | gag | ttc | ctc | gaa | aac | tat | ctg | ctg | act | gat | 864 |
|---|---|---|---|---|---|---|---|---|---|---|---|---|---|---|---|---|
| Asn | Lys | Glu | Leu | Ala | Lys | Glu | Phe | Leu | Glu | Asn | Tyr | Leu | Leu | Thr | Asp | |
| | | 275 | | | | | 280 | | | | | 285 | | | | |

| gaa | ggt | ctg | gaa | gcg | gtt | aat | aaa | gac | aaa | ccg | ctg | ggt | gcc | gta | gcg | 912 |
|---|---|---|---|---|---|---|---|---|---|---|---|---|---|---|---|---|
| Glu | Gly | Leu | Glu | Ala | Val | Asn | Lys | Asp | Lys | Pro | Leu | Gly | Ala | Val | Ala | |
| | 290 | | | | | 295 | | | | | 300 | | | | | |

| ctg | aag | tct | tac | gag | gaa | gag | ttg | gcg | aaa | gat | cca | cgt | att | gcc | gcc | 960 |
|---|---|---|---|---|---|---|---|---|---|---|---|---|---|---|---|---|
| Leu | Lys | Ser | Tyr | Glu | Glu | Glu | Leu | Ala | Lys | Asp | Pro | Arg | Ile | Ala | Ala | |
| 305 | | | | | 310 | | | | | 315 | | | | | 320 | |

| act | atg | gaa | aac | gcc | cag | aaa | ggt | gaa | atc | atg | ccg | aac | atc | ccg | cag | 1008 |
|---|---|---|---|---|---|---|---|---|---|---|---|---|---|---|---|---|
| Thr | Met | Glu | Asn | Ala | Gln | Lys | Gly | Glu | Ile | Met | Pro | Asn | Ile | Pro | Gln | |
| | | | | 325 | | | | | 330 | | | | | 335 | | |

| atg | tcc | gct | ttc | tgg | tat | gcc | gtg | cgt | act | gcg | gtg | atc | aac | gcc | gcc | 1056 |
|---|---|---|---|---|---|---|---|---|---|---|---|---|---|---|---|---|
| Met | Ser | Ala | Phe | Trp | Tyr | Ala | Val | Arg | Thr | Ala | Val | Ile | Asn | Ala | Ala | |
| | | | 340 | | | | | 345 | | | | | 350 | | | |

| agc | ggt | cgt | cag | act | gtc | gat | gaa | gcc | ctg | aaa | gac | gcg | cag | act | aat | 1104 |
|---|---|---|---|---|---|---|---|---|---|---|---|---|---|---|---|---|
| Ser | Gly | Arg | Gln | Thr | Val | Asp | Glu | Ala | Leu | Lys | Asp | Ala | Gln | Thr | Asn | |
| | | 355 | | | | | 360 | | | | | 365 | | | | |

| tcg | agc | tcg | aac | aac | aac | aac | aat | aac | aat | aac | aac | aac | ctc | ggg | ccg | 1152 |
|---|---|---|---|---|---|---|---|---|---|---|---|---|---|---|---|---|
| Ser | Ser | Ser | Asn | Asn | Asn | Asn | Asn | Asn | Asn | Asn | Asn | Asn | Leu | Gly | Pro | |
| 370 | | | | | 375 | | | | | 380 | | | | | | |

| ggt | gcg | gca | cac | tac | gta | gaa | ttc | gga | tcc | atg | gaa | cga | gct | ata | caa | 1200 |
|---|---|---|---|---|---|---|---|---|---|---|---|---|---|---|---|---|
| Gly | Ala | Ala | His | Tyr | Val | Glu | Phe | Gly | Ser | Met | Glu | Arg | Ala | Ile | Gln | |
| 385 | | | | 390 | | | | | 395 | | | | | 400 | | |

| gga | aac | gac | act | agg | gaa | caa | gct | aac | ggt | gaa | cgt | tgg | gat | gga | gga | 1248 |
|---|---|---|---|---|---|---|---|---|---|---|---|---|---|---|---|---|
| Gly | Asn | Asp | Thr | Arg | Glu | Gln | Ala | Asn | Gly | Glu | Arg | Trp | Asp | Gly | Gly | |
| | | | | 405 | | | | | 410 | | | | | 415 | | |

| tca | gga | ggt | atc | act | tct | ccc | ttc | aaa | ctt | cct | gac | gaa | agt | ccg | agt | 1296 |
|---|---|---|---|---|---|---|---|---|---|---|---|---|---|---|---|---|
| Ser | Gly | Gly | Ile | Thr | Ser | Pro | Phe | Lys | Leu | Pro | Asp | Glu | Ser | Pro | Ser | |
| | | | 420 | | | | | 425 | | | | | 430 | | | |

| tgg | act | gag | tgg | cgg | cta | tat | aac | gat | gag | acg | aat | tcg | aat | caa | gat | 1344 |
|---|---|---|---|---|---|---|---|---|---|---|---|---|---|---|---|---|
| Trp | Thr | Glu | Trp | Arg | Leu | Tyr | Asn | Asp | Glu | Thr | Asn | Ser | Asn | Gln | Asp | |
| | | 435 | | | | | 440 | | | | | 445 | | | | |

| aat | ccc | ctt | ggt | ttc | aag | gaa | agc | tgg | ggt | ttc | ggg | aaa | gtt | gta | ttt | 1392 |
|---|---|---|---|---|---|---|---|---|---|---|---|---|---|---|---|---|
| Asn | Pro | Leu | Gly | Phe | Lys | Glu | Ser | Trp | Gly | Phe | Gly | Lys | Val | Val | Phe | |
| 450 | | | | | 455 | | | | | 460 | | | | | | |

| aag | aga | tat | ctc | aga | tac | gac | agg | acg | gaa | gct | tca | ctg | cac | aga | gtc | 1440 |
|---|---|---|---|---|---|---|---|---|---|---|---|---|---|---|---|---|
| Lys | Arg | Tyr | Leu | Arg | Tyr | Asp | Arg | Thr | Glu | Ala | Ser | Leu | His | Arg | Val | |
| 465 | | | | 470 | | | | | 475 | | | | | 480 | | |

| ctt | gga | tct | tgg | acg | gga | gat | tcg | gtt | aac | tat | gca | gca | tct | cga | ttt | 1488 |
|---|---|---|---|---|---|---|---|---|---|---|---|---|---|---|---|---|
| Leu | Gly | Ser | Trp | Thr | Gly | Asp | Ser | Val | Asn | Tyr | Ala | Ala | Ser | Arg | Phe | |
| | | | 485 | | | | | 490 | | | | | 495 | | | |

| ctc | ggt | gcc | aac | cag | gtc | gga | tgt | acc | tat | agt | att | cgg | ttt | cga | gga | 1536 |
|---|---|---|---|---|---|---|---|---|---|---|---|---|---|---|---|---|
| Leu | Gly | Ala | Asn | Gln | Val | Gly | Cys | Thr | Tyr | Ser | Ile | Arg | Phe | Arg | Gly | |
| | | 500 | | | | | 505 | | | | | 510 | | | | |

| gtt | agt | gtc | acc | att | tct | gga | ggg | tcg | aga | act | ctt | cag | cat | ctc | tgt | 1584 |
|---|---|---|---|---|---|---|---|---|---|---|---|---|---|---|---|---|
| Val | Ser | Val | Thr | Ile | Ser | Gly | Gly | Ser | Arg | Thr | Leu | Gln | His | Leu | Cys | |
| | | | 515 | | | | | 520 | | | | | 525 | | | |

| gag | atg | gca | att | cgg | tct | aag | caa | gaa | ctg | tta | cag | ctt | acc | cca | gtc | 1632 |
|---|---|---|---|---|---|---|---|---|---|---|---|---|---|---|---|---|
| Glu | Met | Ala | Ile | Arg | Ser | Lys | Gln | Glu | Leu | Leu | Gln | Leu | Thr | Pro | Val | |
| 530 | | | | | 535 | | | | | 540 | | | | | | |

| gaa | gtg | gaa | agt | aat | gta | tca | aga | gga | tgc | cct | gaa | ggt | att | gaa | acc | 1680 |
|---|---|---|---|---|---|---|---|---|---|---|---|---|---|---|---|---|
| Glu | Val | Glu | Ser | Asn | Val | Ser | Arg | Gly | Cys | Pro | Glu | Gly | Ile | Glu | Thr | |
| 545 | | | | 550 | | | | | 555 | | | | | 560 | | |

| ttc | aag | aaa | gaa | agc | gag | gga | tcc | tct | aga | gtc | gac | ctg | cag | acg | aca | 1728 |

```
Phe Lys Lys Glu Ser Glu Gly Ser Ser Arg Val Asp Leu Gln Thr Thr
                565                 570                 575 aat cct ggt gta tcc gct tgg cag gtc aac aca gct tat act gcg gga    1776
Asn Pro Gly Val Ser Ala Trp Gln Val Asn Thr Ala Tyr Thr Ala Gly
            580                 585                 590 caa ttg gtc aca tat aac ggc aag acg tat aaa tgt ttg cag ccc cac    1824
Gln Leu Val Thr Tyr Asn Gly Lys Thr Tyr Lys Cys Leu Gln Pro His
                595                 600                 605 acc tcc ttg gca gga tgg gaa cca tcc aac gtt cct gcc ttg tgg cag    1872
Thr Ser Leu Ala Gly Trp Glu Pro Ser Asn Val Pro Ala Leu Trp Gln
        610                 615                 620 ctt caa tga                                                        1881
Leu Gln
625

<210> SEQ ID NO 33
<211> LENGTH: 626
<212> TYPE: PRT
<213> ORGANISM: Carnation Italian ringspot virus

<400> SEQUENCE: 33

Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285
```

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Pro
    370                 375                 380

Gly Ala Ala His Tyr Val Glu Phe Gly Ser Met Glu Arg Ala Ile Gln
385                 390                 395                 400

Gly Asn Asp Thr Arg Glu Gln Ala Asn Gly Glu Arg Trp Asp Gly
            405                 410                 415

Ser Gly Gly Ile Thr Ser Pro Phe Lys Leu Pro Asp Glu Ser Pro Ser
        420                 425                 430

Trp Thr Glu Trp Arg Leu Tyr Asn Asp Glu Thr Asn Ser Asn Gln Asp
    435                 440                 445

Asn Pro Leu Gly Phe Lys Glu Ser Trp Gly Phe Gly Lys Val Val Phe
450                 455                 460

Lys Arg Tyr Leu Arg Tyr Asp Arg Thr Glu Ala Ser Leu His Arg Val
465                 470                 475                 480

Leu Gly Ser Trp Thr Gly Asp Ser Val Asn Tyr Ala Ala Ser Arg Phe
            485                 490                 495

Leu Gly Ala Asn Gln Val Gly Cys Thr Tyr Ser Ile Arg Phe Arg Gly
        500                 505                 510

Val Ser Val Thr Ile Ser Gly Gly Ser Arg Thr Leu Gln His Leu Cys
    515                 520                 525

Glu Met Ala Ile Arg Ser Lys Gln Glu Leu Leu Gln Leu Thr Pro Val
530                 535                 540

Glu Val Glu Ser Asn Val Ser Arg Gly Cys Pro Gly Gly Ile Glu Thr
545                 550                 555                 560

Phe Lys Lys Glu Ser Glu Gly Ser Ser Arg Val Asp Leu Gln Thr Thr
            565                 570                 575

Asn Pro Gly Val Ser Ala Trp Gln Val Asn Thr Ala Tyr Thr Ala Gly
        580                 585                 590

Gln Leu Val Thr Tyr Asn Gly Lys Thr Tyr Lys Cys Leu Gln Pro His
    595                 600                 605

Thr Ser Leu Ala Gly Trp Glu Pro Ser Asn Val Pro Ala Leu Trp Gln
    610                 615                 620

Leu Gln
625

<210> SEQ ID NO 34
<211> LENGTH: 34
<212> TYPE: DNA
<213> ORGANISM: unknown
<220> FEATURE:
<223> OTHER INFORMATION: primer

<400> SEQUENCE: 34
gactctgcag acgacaaatc ctggtgtatc cgct                            34

```
<210> SEQ ID NO 35
<211> LENGTH: 37
<212> TYPE: DNA
<213> ORGANISM: unknown
<220> FEATURE:
<223> OTHER INFORMATION: primer

<400> SEQUENCE: 35
taggaagctt tcattgaagc tgccacaagg caggaac                              37
```